(12) United States Patent
Takahashi et al.

(10) Patent No.: US 11,553,829 B2
(45) Date of Patent: Jan. 17, 2023

(54) INFORMATION PROCESSING APPARATUS, CONTROL METHOD AND PROGRAM

(71) Applicants: NEC CORPORATION, Tokyo (JP); NATIONAL CANCER CENTER, Tokyo (JP)

(72) Inventors: Ikuma Takahashi, Tokyo (JP); Maki Sano, Tokyo (JP); Motoyasu Okutsu, Tokyo (JP); Chiemi Tanaka, Tokyo (JP); Masahiro Saikou, Tokyo (JP); Hitoshi Imaoka, Tokyo (JP); Kenichi Kamijo, Tokyo (JP); Yutaka Saito, Tokyo (JP); Masayoshi Yamada, Tokyo (JP)

(73) Assignees: NEC CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 548 days.

(21) Appl. No.: 16/615,160

(22) PCT Filed: May 18, 2018

(86) PCT No.: PCT/JP2018/019310
§ 371 (c)(1),
(2) Date: Nov. 20, 2019

(87) PCT Pub. No.: WO2018/216618
PCT Pub. Date: Nov. 29, 2018

(65) Prior Publication Data
US 2020/0170485 A1 Jun. 4, 2020

(30) Foreign Application Priority Data
May 25, 2017 (JP) .............................. JP2017-103349

(51) Int. Cl.
*A61B 1/00* (2006.01)
*G16H 30/40* (2018.01)
(Continued)

(52) U.S. Cl.
CPC ...... *A61B 1/00055* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS

| 10,334,155 B2 | 6/2019 | Hasebe |
| 2006/0020295 A1 | 1/2006 | Brockway et al. |

(Continued)

FOREIGN PATENT DOCUMENTS

| CN | 1305774 A | 8/2001 |
| CN | 1615800 A | 5/2005 |

(Continued)

OTHER PUBLICATIONS

International Search Report of PCT/JP2018/019310 dated Jul. 10, 2018 [PCT/ISA/210].

(Continued)

*Primary Examiner* — Delomia L Gilliard
(74) *Attorney, Agent, or Firm* — Sughrue Mion, PLLC

(57) ABSTRACT

An information processing apparatus (2000) detects an abnormal region (30) from a predetermined range (16) of a video frame (14). The information processing apparatus (2000) determines whether a predetermined condition is satisfied in a case where the abnormal region (30) is detected from the predetermined range (16) of a certain video frame (14) and the abnormal region (30) is not detected from the predetermined range (16) of a predetermined video frame (Continued)

(14) generated later than the video frame (14). In a case where the predetermined condition is not satisfied, the information processing apparatus (2000) performs a predetermined notification.

23 Claims, 19 Drawing Sheets

(51) Int. Cl.
*A61B 1/04* (2006.01)
*G06T 7/00* (2017.01)

(52) U.S. Cl.
CPC .............. *A61B 1/04* (2013.01); *G06T 7/0016* (2013.01); *G16H 30/40* (2018.01); *G06T 2207/10068* (2013.01); *G06T 2207/30096* (2013.01)

(56) References Cited

U.S. PATENT DOCUMENTS

| | | | |
|---|---|---|---|
| 2007/0268280 A1* | 11/2007 | Fujita | A61B 1/00045 345/204 |
| 2008/0009669 A1* | 1/2008 | Ozawa | A61B 1/00045 600/101 |
| 2008/0058593 A1 | 3/2008 | Gu et al. | |
| 2008/0119691 A1 | 5/2008 | Yagi et al. | |
| 2011/0254937 A1 | 10/2011 | Yoshino | |
| 2016/0241800 A1* | 8/2016 | Shin | G02B 23/2484 |
| 2018/0098690 A1 | 4/2018 | Iwaki | |
| 2018/0249900 A1* | 9/2018 | Imaizumi | A61B 1/045 |
| 2019/0069757 A1 | 3/2019 | Iwaki | |
| 2019/0365200 A1* | 12/2019 | Tatsuta | A61B 5/0064 |
| 2020/0129042 A1* | 4/2020 | Takahashi | A61B 1/045 |

FOREIGN PATENT DOCUMENTS

| | | |
|---|---|---|
| CN | 1649311 A | 8/2005 |
| CN | 101523263 A | 9/2009 |
| CN | 102056530 A | 5/2011 |
| CN | 102247116 A | 11/2011 |
| CN | 102421916 A | 4/2012 |
| CN | 103250406 A | 8/2013 |
| CN | 103442628 A | 12/2013 |
| CN | 104814862 A | 8/2015 |
| CN | 105247074 A | 1/2016 |
| CN | 105249549 A | 1/2016 |
| CN | 105916262 A | 8/2016 |
| EP | 1 862 106 A1 | 12/2007 |
| EP | 2 937 033 A4 | 2/2017 |
| JP | 2007-159934 A | 6/2007 |
| JP | 2010-512173 A | 4/2010 |
| JP | 2010-172673 A | 8/2010 |
| JP | 2010-282519 A | 12/2010 |
| JP | 2011-22857 A | 2/2011 |
| JP | 2011-036371 A | 2/2011 |
| JP | 2012-170774 A | 9/2012 |
| JP | 2016-048426 A | 4/2016 |
| JP | 2016-202722 A | 12/2016 |
| WO | 2011/132468 A1 | 10/2011 |
| WO | 2016/199273 A1 | 12/2016 |
| WO | 2017/081976 A1 | 5/2017 |

OTHER PUBLICATIONS

Notice of Allowance dated Nov. 17, 2021 in Chinese Application No. 201880034276.8.
Nowinski et al., "Three-Dimensional Interactive Atlas of Cranial Nerve-Related Disorders", Neuroradiol J., 2013, vol. 26, No. 3, pp. 263-275 (8 pages total).
Office Action dated May 31, 2021 by the Chinese Patent Office in Chinese Application No. 201880034276.8.
Peng Li et al., "Early colorectal cancer and pre-cancer screening and diagnosis and treatment consensus in China", Chinese Journal of Practical Medicine, 2015, vol. 35, No. 3, pp. 211-227 (17 pages).
Matthew L. White et al., "Primary angiitis of the central nervous system: apparent diffusion coefficient lesion analysis", Clinical Imaging, 2010, vol. 34, pp. 1-6 (6 pages).
Extended European Search Report dated Feb. 8, 2021 from the European Patent Office in EP Application No. 18806136.0.

* cited by examiner

HALF-TONE DOT MESHING

DOT PATTERN

MARK SHOWING
CENTER POSITION

RECTANGULAR FRAME

BOUNDARY FRAME

ELLIPTIC FRAME

HIGHLIGHT VIDEO FRAME INCLUDING SAME ABNORMAL
REGION AS ABNORMAL REGION INCLUDED IN VIDEO FRAME

FIG. 19

| ABNORMAL REGION DISCRIMINATOR | DATA |
|---|---|
| r001 | (v1, img001), (v5, img005) |
| r002 | (v2, img2), (v4, img4) |
| r003 | (v3, img3) |

INFORMATION PROCESSING APPARATUS, CONTROL METHOD AND PROGRAM

CROSS REFERENCE TO RELATED APPLICATIONS

This application is a National Stage of International Application No. PCT/JP2018/019310, filed May 18, 2018, claiming priority to Japanese Patent Application No. 2017-103349, filed May 25, 2017, the contents of all of which are incorporated herein by reference in their entirety.

TECHNICAL FIELD

The present invention relates to an information processing apparatus, a control method, and a program.

BACKGROUND ART

An examination is performed to find out whether there is an abnormality in a body by using an image in which an inside of the body of a person or an animal is imaged. For example, Patent Documents 1 to 3 disclose a technique of displaying side by side an image (CT image or MRI image) obtained in a past examination (for example, one year ago) and an image obtained in a present examination. Further, Patent Documents 1 and 4 disclose a technique of detecting a lesion from an image and marking the detected lesion.

RELATED DOCUMENT

Patent Document

[Patent Document 1] Japanese Patent Application Publication No. 2007-159934
[Patent Document 2] Japanese Patent Application Publication No. 2016-048426
[Patent Document 3] Japanese Patent Application Publication No. 2016-202722
[Patent Document 4] PCT Publication No. WO 2011/132468

SUMMARY OF THE INVENTION

Technical Problem

As one of methods for examining an inside of the body, there is a method to examine a state of the inside of the body by viewing a video displayed on a display device using an endoscope system or the like. Specifically, a doctor inserts a scope that has a camera at a tip from a nose, mouth, anus, or the like of a subject, and moves the scope in the body. By doing so, the state inside the body is imaged by the camera. The doctor checks whether there is an abnormal site in the body of the subject while viewing the state of the inside of the body imaged by the camera using the video displayed on the display device.

As described above, in the method in which the examination is performed by moving the camera in the body of the subject, a site that can be observed by the doctor changes over time since the camera is moved in the body. Therefore, the doctor may miss the abnormal site, and there is actually a difference in the lesion detection rate depending on doctors in charge of the examination. In each related document described above, a situation where the site that can be observed by the doctor changes over time in this manner is not assumed.

The present invention is made in view of the above problems. One of the objects of the present invention is to provide a technique for improving the quality of an examination using a video in which an inside of the body of a subject is imaged.

Solution to Problem

An information processing apparatus according to the present invention includes: 1) a detection unit that detects an abnormal region of an inside of a body from a video in which the inside of the body is imaged; 2) a determination unit that determines whether a predetermined condition is satisfied in a case where the abnormal region is detected from in a predetermined range in a first video frame of the video and the abnormal region is not detected from in the predetermined range in a second video frame of the video generated later than the first video frame; and 3) a notification unit that performs a first notification in a case where the predetermined condition is determined to be not satisfied.

A control method of the present invention is executed by a computer. The control method includes: 1) a detection step of detecting an abnormal region of an inside of a body from a video in which the inside of the body is imaged; 2) a determining step of determining whether a predetermined condition is satisfied in a case where the abnormal region is detected from in a predetermined range of a first video frame of the video and the abnormal region is not detected from in the predetermined range of a second video frame of the video generated later than the first video frame; and 3) a notification step of performing a first notification in a case where the predetermined condition is determined to be not satisfied.

A program of the present invention causes a computer to execute each step of the control method of the present invention.

Advantageous Effects of Invention

According to the present invention, there is provided a technique for improving the accuracy of an examination using a video in which a body of a subject is imaged.

BRIEF DESCRIPTION OF THE DRAWINGS

The objects described above, and other objects, features and advantages will become more apparent from preferred example embodiments described below and the following drawings accompanying the example embodiments.

FIG. 19 is a diagram illustrating history information in a table format.

DESCRIPTION OF EMBODIMENTS

Figure 1A:
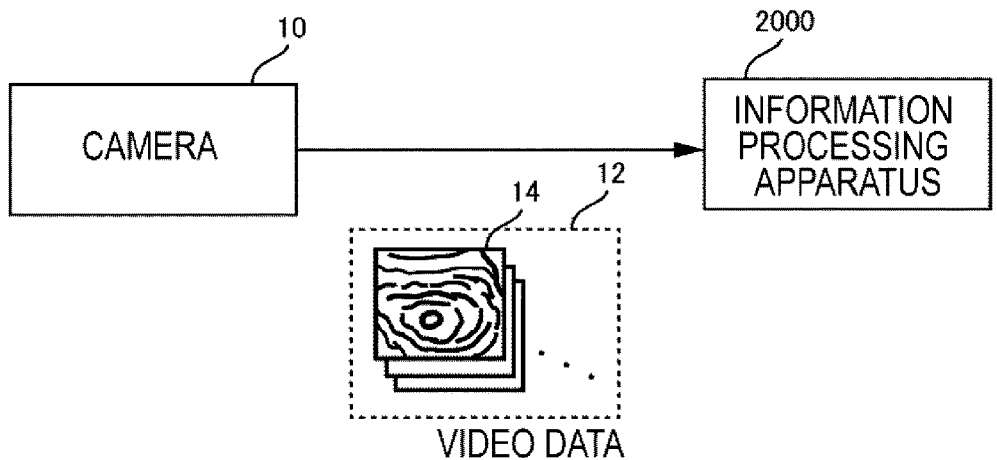
FIGS. 1A and 1B are diagrams conceptually illustrating an information processing apparatus according to an example embodiment 1.

Hereinafter, embodiments of the present invention will be described with reference to the drawings. Note that, in all the drawings, the same reference numeral is assigned to the same component and the description thereof will not be repeated. In each block diagram, each block represents a configuration of a function unit, not a configuration of a hardware unit, unless otherwise described.

Example Embodiment 1

Figure 1B:
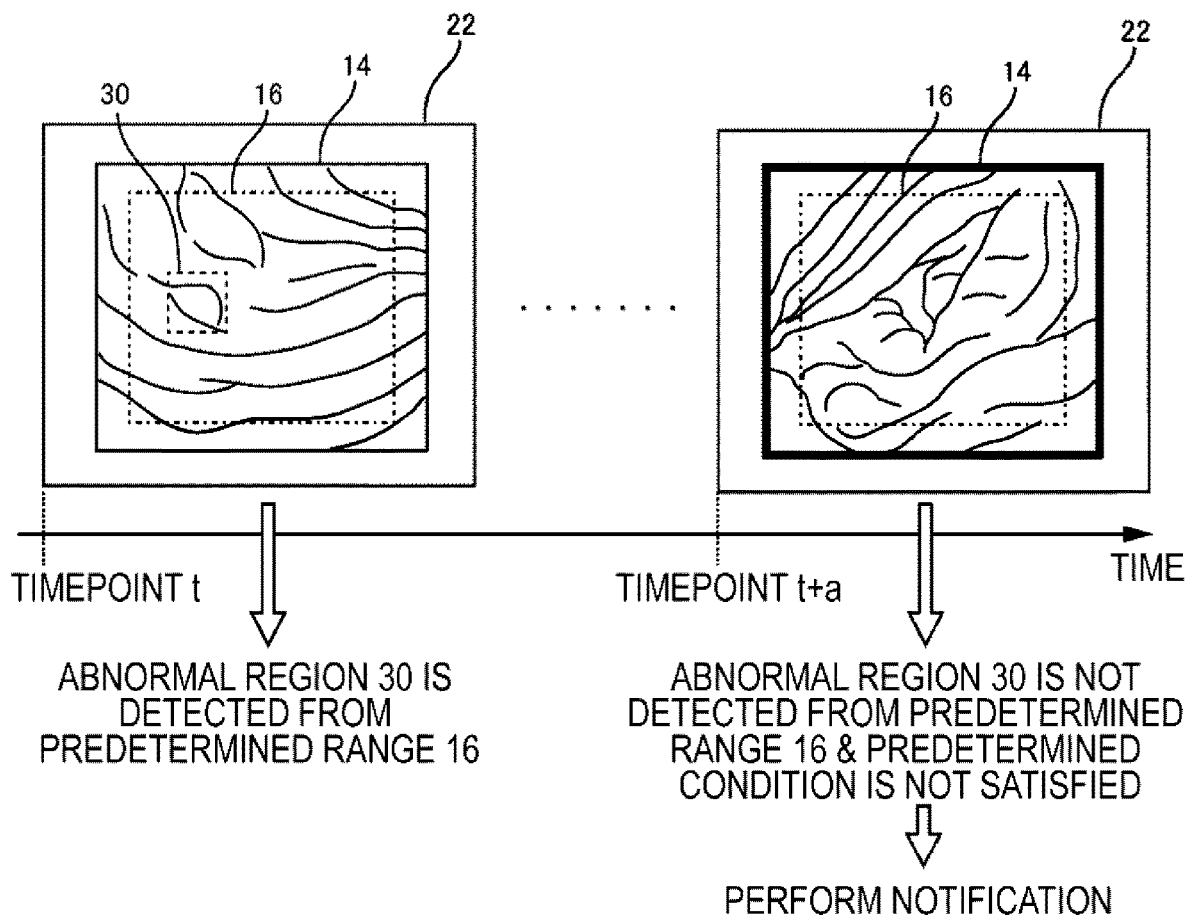

FIGS. 1A and 1B are diagrams conceptually illustrating an information processing apparatus 2000 according to an example embodiment 1. FIG. 1A conceptually shows a usage environment of the information processing apparatus 2000. FIG. 1B conceptually shows an operation of the information processing apparatus 2000. Note that FIGS. 1A and 1B only show examples of the operation thereof for ease of understanding the information processing apparatus 2000, and do not limit functions of the information processing apparatus 2000.

A camera 10 is used for examining people or other animals. Hereinafter, a person to be examined is referred to as a subject. The camera 10 is any camera capable of imaging the inside of the body of the subject and generates a video frame 14 representing the imaging result. For example, the camera 10 is an endoscope camera. Video data 12 is composed of a plurality of video frames 14 generated at mutually different times.

The video data 12 generated by the camera 10 is displayed on a display device 20. The display device 20 is any display device capable of displaying the video data 12. Note that displaying the video data 12 on the display device 20 means that displaying the plurality of video frames 14 constituting the video data 12 on the display device 20 in order.

A user (for example, doctor) of the information processing apparatus 2000 recognizes a state of the inside of the subject's body by viewing the video data 12 displayed on the display device 20. More specifically, the user recognizes whether there is an abnormal site in the body of the subject, a degree of the abnormality, and the like. Here, the "abnormal site in the body" is, for example, a site having a lesion, a site having a wound, or a site having a foreign object. The lesion is a change in a living body caused by a disease, such as a tumor.

Here, in an endoscope examination or the like for searching for the abnormal site in the body while the inside of the subject's body is observed by the camera, a doctor may miss the abnormal site even though the abnormal site is imaged by the camera. Therefore, it is preferable to provide support such that the doctor can easily recognize the abnormal site and thus to avoid missing of the abnormal site.

The information processing apparatus 2000 according to the present example embodiment performs the following operation. First, the information processing apparatus 2000 acquires the video data 12 and performs an image analysis of the video frame 14 constituting the video data 12. Specifically, the information processing apparatus 2000 detects an abnormal region 30 from a predetermined range 16 of the video frame 14. The abnormal region 30 is a region estimated to represent the abnormal site in the body of the subject. For example, the abnormal region 30 in FIG. 1B is a region including the tumor (region representing the lesion). The predetermined range 16 may be an entire video frame 14 or an image region smaller than the entire video frame 14 (a part of the image region of the video frame 14).

Here, it is assumed that the abnormal region 30 is detected from the predetermined range 16 of a video frame 14 and the abnormal region 30 is not detected from the predetermined range 16 of a video frame 14 generated later than the video frame 14. In other words, it is assumed that the abnormal region 30 falls in (frames in) all or a part of an imaging range of the camera 10 and then goes out (frames out) from all or part of the imaging range of the camera 10.

In this case, the information processing apparatus 2000 determines whether a predetermined condition is satisfied. In a case where the predetermined condition is not satisfied, a predetermined notification (hereinafter referred to as a first notification) is performed. The predetermined condition is a condition that is satisfied in a case where it is estimated that the user of the information processing apparatus 2000 recognizes the abnormal region 30 included in the video data 12. In other words, the predetermined condition is a condition that is not satisfied in a case where it is estimated that the user of the information processing apparatus 2000 does not recognize the abnormal region 30 included in the video data 12.

The operation of the above information processing apparatus 2000 will be described using FIG. 1B. Note that the predetermined range 16 is displayed as a dotted line in FIG. 1B for the purpose of explanation, but a frame line representing the predetermined range 16 is not necessarily to be displayed on the display device 20. The same applies to the subsequent figures.

FIG. 1B shows a screen displayed on the display device 20 at timepoint t and a screen displayed on the display device 20 at timepoint t+a thereafter. The abnormal region 30 is included in the predetermined range 16 of the video frame 14 displayed on the display device 20 at timepoint t. On the other hand, the abnormal region 30 is not included in the predetermined range 16 of the video frame 14 displayed on the display device 20 at timepoint t+a.

The information processing apparatus 2000 determines whether the predetermined condition described above is satisfied. Here, it is assumed that the predetermined condition is not satisfied in the example of FIG. 1B. That is, it is estimated that the user does not recognize the abnormal region 30. Accordingly, the information processing apparatus 2000 performs the first notification described above. For example, in FIG. 1, the first notification is performed in which the frame line of the video frame 14 is thickened and highlighted.

With such an operation of the information processing apparatus 2000, in a case where it is estimated that the abnormal region 30 becomes not included in the predetermined range of the video data 12 and the user does not recognize the abnormal region 30, the notification is performed. By doing this, it is possible for the user to be aware of the presence of the unrecognized abnormal region 30, and thus it is possible to prevent the user from missing the abnormal region 30. Accordingly, it is possible to improve the accuracy of the examination of the inside of the body performed using the camera 10.

Hereinafter, the present example embodiment will be described in more detail.

<Functional Configuration>

Figure 2:
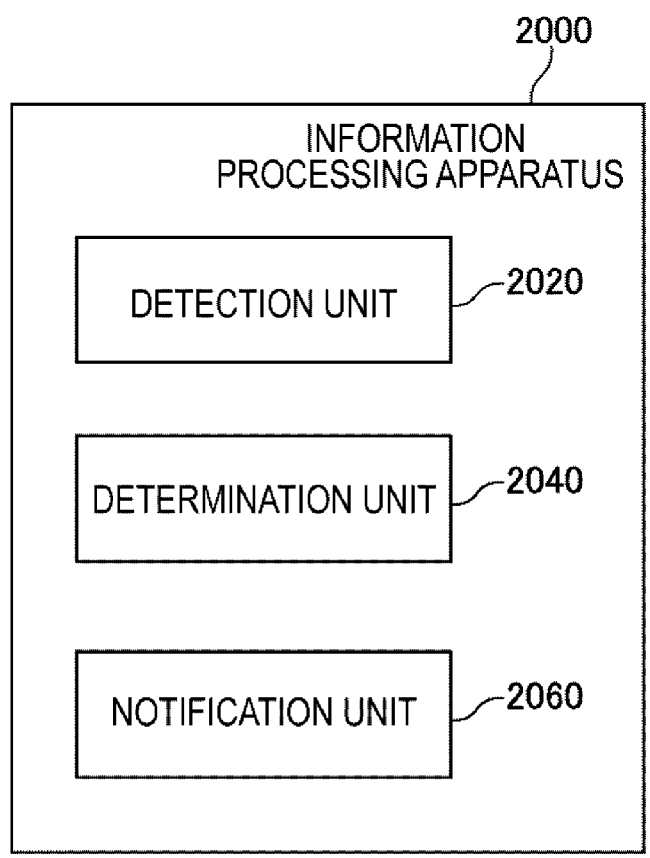
FIG. 2 is a block diagram illustrating a functional configuration of the information processing apparatus.

FIG. 2 is a block diagram illustrating a functional configuration of the information processing apparatus 2000. The information processing apparatus 2000 has a detection unit 2020, a determination unit 2040, and a notification unit 2060. The detection unit 2020 detects the abnormal region 30 from the video data 12. The determination unit 2040 determines whether the predetermined condition described above is satisfied in a case where the abnormal region 30 is detected from the predetermined range 16 of a certain video frame 14 (referred to as a first video frame) of the video data 12 and the abnormal region 30 is not detected from the predetermined range 16 of a video frame 14 (referred to as a second video frame) generated later than the video frame 14. The notification unit 2060 performs the first notification described above when it is determined that the predetermined condition is not satisfied.

<Example of Hardware Configuration of Information Processing Apparatus 2000>

Each functional configuration unit of the information processing apparatus 2000 may be formed by hardware (for example, a hard-wired electronic circuit or the like) that forms each functional configuration unit or a combination of hardware and software (for example, a combination of an electronic circuit and a program that controls the circuit). Hereinafter, the case where each functional configuration unit of the information processing apparatus 2000 is formed by the combination of hardware and software will be further described.

Figure 3:
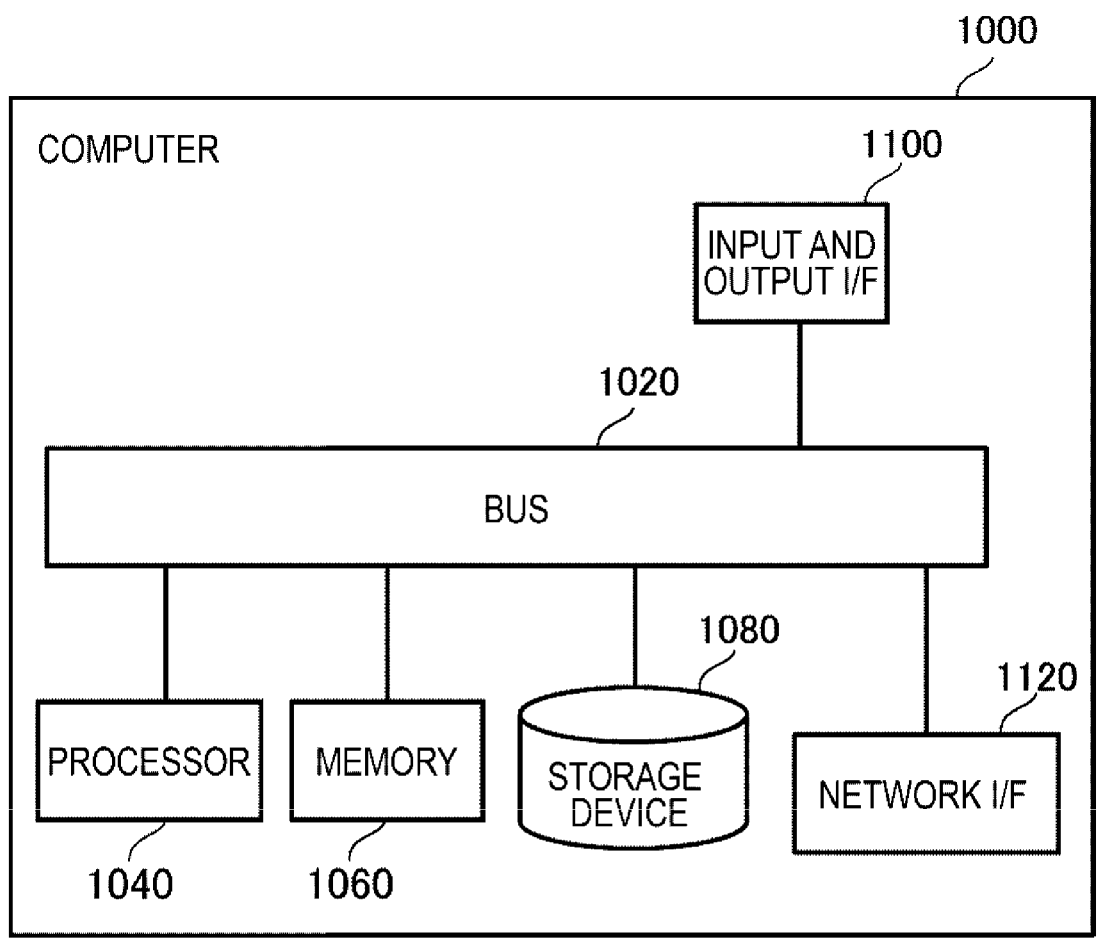
FIG. 3 is a diagram illustrating a computer for forming the information processing apparatus.

FIG. 3 is a diagram illustrating a computer 1000 for forming the information processing apparatus 2000. The computer 1000 is a variety of computers. For example, the computer 1000 is a personal computer (PC), a server machine, a tablet terminal, a smartphone, or the like. The computer 1000 may be a dedicated computer designed to form the information processing apparatus 2000 or may be a general-purpose computer.

The computer 1000 has a bus 1020, a processor 1040, a memory 1060, a storage device 1080, an input and output interface 1100, and a network interface 1120. The bus 1020 is a data transmission path for the processor 1040, the memory 1060, the storage device 1080, the input and output interface 1100, and the network interface 1120 to mutually transmit and receive data. The processor 1040 is an arithmetic processing apparatus such as a central processing unit (CPU) or a graphics processing unit (GPU). The memory 1060 is a main storage device formed by a random access memory (RAM) or the like. The storage device 1080 is an auxiliary storage device formed by a hard disk, a solid state drive (SSD), a ROM, or a memory card. However, the storage device 1080 may be formed by hardware similar to the hardware used to form the main storage device, such as the RAM.

The input and output interface 1100 is an interface for connecting the computer 1000 to an input and output device. For example, the camera 10 and the display device 20 are connected to the input and output interface 1100.

The network interface 1120 is an interface for connecting to a communication network such as a wide area network (WAN) or a local area network (LAN).

The storage device 1080 stores a program module for realizing each function of the information processing apparatus 2000. The processor 1040 reads each of the program modules into the memory 1060 and executes each program module to realize each function corresponding to the program module.

<Specific Example of Usage Environment of Information Processing Apparatus 2000>

Figure 4:
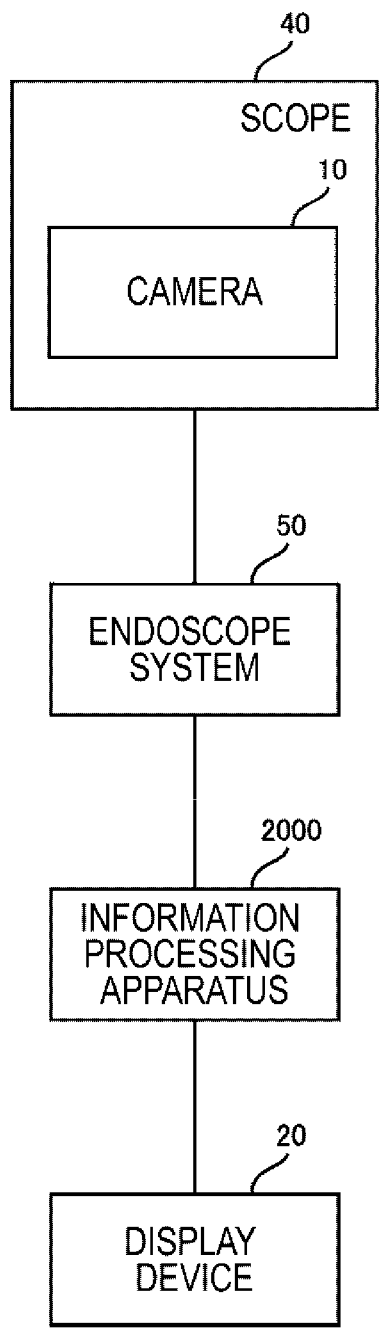
FIG. 4 is a diagram illustrating a specific example of a usage environment of the information processing apparatus.

FIG. 4 is a diagram showing a specific example of a usage environment of the information processing apparatus 2000. For example, the information processing apparatus 2000 is used together with a scope 40 and an endoscope system 50. The scope 40 is connected to the endoscope system 50. The scope 40 is provided with the camera 10. In this case, the video data 12 is composed of the plurality of video frames 14 generated by the camera 10 provided in the scope 40. The endoscope system 50 outputs the video data 12 to the information processing apparatus 2000. For example, the video data 12 is output from an interface for video output (for example, High-Definition Multimedia Interface (HDMI) (registered trademark) interface) provided in the endoscope system 50 to an interface for video input of the information processing apparatus 2000. The information processing apparatus 2000 processes the video data 12 acquired from the endoscope system 50 to perform the first notification.

Here, as described below, the first notification may be a display performed using the display device 20 or may be other than that. In the former case, the information processing apparatus 2000 controls the display device 20 to display the video data 12 including the first notification on the display device 20. On the other hand, in the latter case, the processing of displaying the video data 12 on the display device 20 may be performed by the information processing apparatus 2000 or may be performed by another apparatus (for example, the endoscope system 50). In a case where the processing of displaying the video data 12 on the display device 20 is performed by the endoscope system 50, it is not necessary for the display device 20 to be connected to the information processing apparatus 2000.

Note that the configuration shown in FIG. 4 is merely an example, and the usage environment of the information processing apparatus 2000 is not limited to the configuration shown in FIG. 4. For example, the video data 12 may be output from the camera 10 to the information processing apparatus 2000. In this case, the information processing apparatus 2000 may not be connected to the endoscope system 50.

<Flow of Processing>

Figure 5:
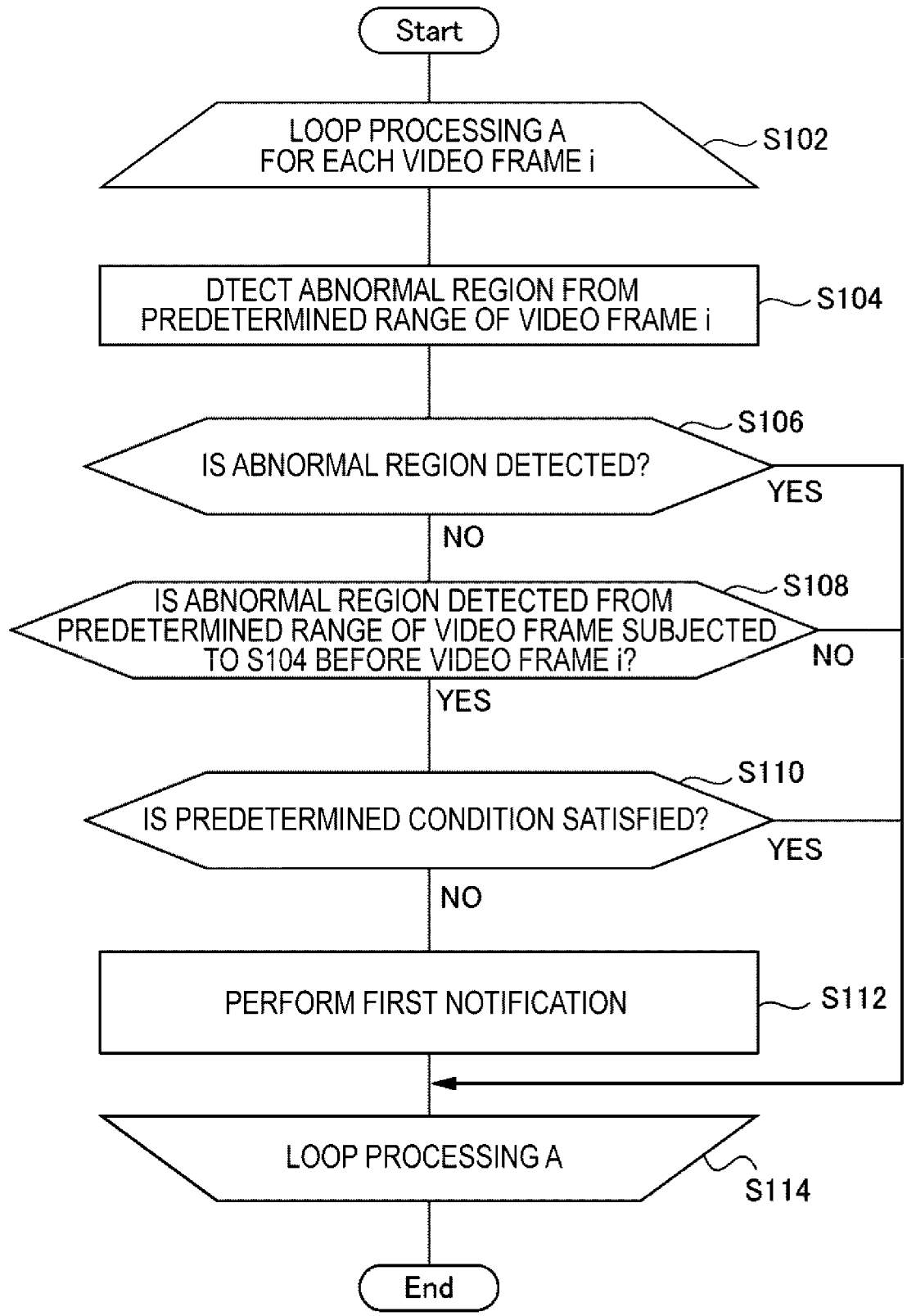
FIG. 5 is a flowchart illustrating a flow of processing executed by the information processing apparatus according to the example embodiment 1.

FIG. 5 is a flowchart illustrating a flow of processing executed by the information processing apparatus 2000 according to the example embodiment 1. Steps S102 to S114 are loop processing executed for each video frame 14 acquired from the camera 10. In S102, the information processing apparatus 2000 selects a video frame 14 with the earliest generation timepoint among the video frames 14 not yet subjected to loop processing A. The video frame 14 selected here is denoted as a video frame i. Note that in a case where the loop processing A is already executed on all the video frames 14, for example, the information processing apparatus 2000 waits until a new video frame 14 is generated. In addition, in this case, the processing of FIG. 5 may be ended.

The detection unit 2020 detects the abnormal region 30 from the predetermined range 16 of the video frame i (S104). In a case where the abnormal region 30 is detected from the predetermined range 16 of the video frame i (YES in S106), the processing of FIG. 5 proceeds to S114. In a case where the abnormal region 30 is not detected from the predetermined range 16 of the video frame i (NO in S106), the determination unit 2040 determines whether the abnormal region 30 is detected from the predetermined range 16 of the video frames subjected to S104 before the video frame i (S108). In a case where the abnormal region 30 is not detected from the predetermined range 16 of the video frames subjected to S104 before the video frame i (NO in S108), the processing of FIG. 5 proceeds to S114.

In a case where the abnormal region 30 is detected from the predetermined range 16 of a video frame subjected to S104 before the video frame i (YES in S108), the determination unit 2040 determines whether the predetermined condition is satisfied (S110). In a case where the predetermined condition is not satisfied (NO in S110), the notification unit 2060 performs the first notification (S112). On the other hand, in a case where the predetermined condition is satisfied (YES in S110), the processing of FIG. 5 proceeds to S114.

S114 is the end of the loop processing A. Therefore, the processing of FIG. 5 proceeds to S102 after S114.

Note that the video frame 14 to be subjected to the processing (S104) of detecting the abnormal region 30 may be all the video frames 14 included in the video data 12 or may be some of the video frames 14. In the latter case, for example, the detection unit 2020 executes S104 only for one video frame 14 for each predetermined number (for example, one for every 10).

<Acquisition of Video Data 12: S102>

Any method of the detection unit 2020 acquiring the video data 12 may be employed. For example, the detection unit 2020 accesses a storage device in which the video data 12 is stored to acquire the video data 12. The storage device in which the video data 12 is stored may be provided inside the camera 10 or may be provided outside the camera 10. For example, the detection unit 2020 may receive the video data 12 transmitted from the camera 10 to acquire the video data 12. Furthermore, the detection unit 2020 may acquire the video data 12 from another apparatus (for example, the above endoscope system 50) connected to the camera 10.

<Detection of Abnormal Region 30: S104>

The detection unit 2020 detects the abnormal region 30 from each video frame 14 constituting the video data 12. Here, an existing technique can be used for a technique of analyzing the image in which the inside of the body is imaged and detecting the abnormal site. For example, a technique such as feature matching or template matching can be used. For example, in a case where the tumor is detected by the feature matching, one or more values (feature values) representing a feature of an appearance (color, pattern, or shape) of the tumor are defined in advance. The detection unit 2020 detects, from the video frame 14, an image region with high similarity with the feature value of the tumor set in advance in the image region of the video frame 14. The detection unit 2020 handles the detected image region as an image region representing the abnormal region 30. The same method can be employed for a case where a flaw or a foreign object is detected.

Note that in the case where a foreign object is desired to be detected, it is assumed that the foreign object that entered into the body has been determined. In this case, it is preferable to be able to specify a feature value of the foreign object to the information processing apparatus 2000. For example, a photograph of the foreign object that was entered into the body is input to the information processing apparatus 2000. The information processing apparatus 2000 performs the image analysis of the photograph to compute the feature value of the foreign object to be detected. The detection unit 2020 detects the foreign object having the computed feature value from the video frame 14.

<Decision by Determination Unit 2040>

The determination unit 2040 determines that the abnormal region 30 detected from the predetermined range 16 of the first video frame is not detected from the predetermined range 16 of the video frame 14 generated thereafter (S106). In other words, the determination unit 2040 determines the second video frame among the video frames 14 generated later than the first video frame, the abnormal region 30 detected from the predetermined range 16 of the first video frame being not detected from the predetermined range 16 of the second video frame 14.

For example, the determination unit 2040 performs tracking of the abnormal region 30. Specifically, the determination unit 2040 performs the tracking of the abnormal region 30 detected from the predetermined range 16 of the first video frame in each video frame 14 generated thereafter. The determination unit 2040 determines the video frame 14 whose predetermined range 16 does not include the abnormal region 30 to be tracked, as the second video frame. Note that in a case where an abnormal region 30 is detected from a certain video frame 14 and the abnormal region 30 has not been tracked until then, the determination unit 2040 handles the video frame 14 as the first video frame. An existing technique can be used for a technique of tracking an object detected from video data. Note that the determination unit 2040 may track an image region representing the abnormal region 30 or may track an image region having a predetermined size or shape including the periphery of the abnormal region 30. The determination unit 2040 may track an image region of the periphery of the abnormal region 30 instead of the abnormal region 30.

Note that a method of determining the second frame by the determination unit 2040 is not limited to the tracking. For example, the determination unit 2040 searches for the feature value of the image region representing the abnormal region 30 detected from the predetermined range 16 of the first video frame in the predetermined range 16 of each video frame 14 generated thereafter, and handles one of the video frames 14 not including the image region having the feature value as the second video frame.

<Determine Whether Predetermined Condition is Satisfied: S110>

In a case where the abnormal region 30 is detected from the predetermined range 16 of a certain video frame 14 (YES in S106) and then the abnormal region 30 is not detected from the predetermined range 16 of a video frame 14 generated later than the video frame 14 (NO in S108), the determination unit 2040 determines whether the above predetermined condition is satisfied (S110). Various conditions can be employed as the predetermined condition. Hereinafter, this predetermined condition is illustrated. Note that the predetermined range 16 can be any range included in the image region of the video frame 14 and can be the entire screen region of the video frame 14, unless otherwise stated. A range in the video frame 14 represented as the predetermined range 16 may be set in advance in the information processing apparatus 2000 or may be stored in a storage device accessible from the information processing apparatus 2000.

Example 1 of Predetermined Condition

In a case where the abnormal region 30 included in the video data 12 is recognized by the user, there is a high probability that the user intends to observe the abnormal region 30 in detail by stopping the movement of the camera 10 or slowing a movement velocity of the camera 10. Accordingly, in the case where the abnormal region 30 is recognized by the user, the movement velocity of the abnormal region 30 in the video data 12 is considered to be relatively slow. In other words, in a case where the abnormal region 30 is not recognized by the user, the movement velocity of the abnormal region 30 in the video data 12 is considered to be relatively fast.

Thus, for example, the predetermined condition is set as "a statistical value representing magnitude of the movement velocity of the abnormal region 30 included in the predetermined range 16 is equal to or less than a predetermined value in the video data 12 from the first video frame to the second video frame". The statistical value representing the magnitude of the movement velocity is, for example, a minimum value, a maximum value, or an average value. The predetermined value may be set in advance in the determination unit 2040 or may be stored in a storage device accessible from the determination unit 2040.

With this predetermined condition, in a case where the movement velocity of the abnormal region 30 from the first video frame to the second video frame is relatively slow, the first notification by the notification unit 2060 is not performed. Accordingly, for example, in a case where the user recognizes the abnormal region 30 and slows down the movement velocity of the camera 10 or temporarily stops the movement of the camera 10, the first notification by the notification unit 2060 is not performed. On the other hand, in a case where the movement velocity of the abnormal region 30 from the first video frame to the second video frame is fast, the first notification by the notification unit 2060 is performed. Accordingly, for example, in a case where the user does not recognize the abnormal region 30 and continues to move the camera 10 fast, the first notification by the notification unit 2060 is performed. Accordingly, it is possible to prevent the user from missing the abnormal region 30.

Note that an existing technique can be used for a technique of computing the movement velocity of an object (abnormal region 30 in the present invention) detected from video data by analyzing the video data.

Example 2 of Predetermined Condition

In the case where the abnormal region 30 included in the video data 12 is recognized by the user, there is a high probability that the user takes some actions. Thus, for example, the above predetermined condition is set as "a predetermined action by the user on the abnormal region 30 is detected after the abnormal region 30 is detected from the predetermined range 16 of the first video frame and before the abnormal region 30 is determined to be not detected from the predetermined range 16 of the second video frame". In a case where the predetermined action by the user is detected after the abnormal region 30 is detected from the predetermined range 16 of the first video frame and before the abnormal region 30 is determined to be not detected from the predetermined range 16 of the second video frame, the determination unit 2040 determines that the predetermined condition is satisfied. Accordingly, the first notification by the notification unit 2060 is not performed. On the other hand, in a case where the predetermined action by the user is not detected in the above period, the determination unit 2040 determines that the above predetermined condition is not satisfied. Accordingly, the first notification by the notification unit 2060 is performed.

Various actions can be employed as the predetermined action described above. For example, the user who has recognized the abnormal region 30 may perform an input operation, such as a keyboard input or pressing of a shutter button, in order to record the video frame 14 including the abnormal region 30 in the storage device. Such an input operation that records the video frame 14 in the storage device is assumed to be the predetermined action.

Note that an existing technique can be used for a technique of recognizing such a predetermined input operation. The determination unit 2040 handles all the abnormal regions 30 included in the predetermined range 16 of the video frame 14 stored in the storage device as a target of the above input operation.

In another example, the user who has recognized the abnormal region 30 may perform a character input operation in order to record an opinion or the like relating to the abnormal region 30. Such a character input operation is assumed to be the above predetermined action. An existing technique can be used for a technique of recognizing such a character input operation.

Here, in a case where the above character input operation is performed by specifying a determined abnormal region 30, the determination unit 2040 handles the specified abnormal region 30 as an abnormal region 30 targeted for the predetermined action by the user. On the other hand, in a case where the above character input operation is performed without specifying the abnormal region 30, for example, the determination unit 2040 handles all the abnormal regions 30 included in the predetermined range 16 of the video frame 14 when the character input operation is performed as abnormal regions 30 targeted for the predetermined action by the user.

In another example, the user who has recognized the abnormal region 30 may perform an input operation of pointing the abnormal region 30 or the periphery thereof using a pointing device such as a mouse. For example, in a case where the doctor provides the subject with explanation regarding the abnormal region 30 during the examination, it is considered that the doctor performs the explanation while pointing the abnormal region 30 displayed on the display device 20. The operation of pointing the abnormal region 30 or the periphery thereof in this manner is assumed to be the above predetermined action.

Note that an existing technique can be used for a technique of recognizing such a pointing operation. The determination unit 2040 handles the abnormal region 30 pointed by the pointing operation as an abnormal region 30 targeted for the predetermined action by the user.

In another example, the user who has recognized the abnormal region 30 may perform 1) an action of changing a color or intensity of light irradiated to the abnormal region 30 or the periphery thereof, 2) an action of performing dye spraying or coloring in the abnormal region 30 or the periphery thereof, 3) an action of administering a medicine to the abnormal region 30 or the periphery thereof, 4) an action of collecting a tissue of the abnormal region 30 or the periphery thereof, or the like. For example, such an action is assumed to be the predetermined action.

The actions 1) to 4) are performed by the user performing a predetermined input operation on the endoscope system or the like. For example, in a common endoscope system, a scope provided with a camera is provided with a mechanism for irradiating light (such as a light source), a mechanism for spraying dye or coloring solution, a mechanism for administering water or a medicine, a mechanism for collecting a tissue, and the like. These mechanisms operate in response to a predetermined input operation that is performed on the endoscope system by the user. In other words, when the various actions described above are performed, an input operation for operating a mechanism that realizes the action is performed.

For example, the determination unit 2040 detects that the input operation for operating these mechanisms is performed, in order to detect that the predetermined action is performed by the user. For example, the determination unit 2040 receives a notification indicating that the input operation is performed from the endoscope system or the like, in order to detect that the input operation is performed.

Here, the determination unit 2040 handles the abnormal region 30 (abnormal region 30 imaged by the camera 10) included in the predetermined range 16 of the video frame 14 displayed on the display device 20 at a timing when the input operation is detected, as an abnormal region 30 targeted for the predetermined action by the user. In other words, the determination unit 2040 handles the abnormal region 30 included in the predetermined range 16 of the video frame 14 whose generation timepoint is the closest to the timepoint at which the input operation is detected, as an abnormal region 30 targeted for the predetermined action by the user.

Note that a method of the determination unit 2040 detecting the actions 1) to 4) is not limited to the above method of detecting the input operation. For example, the determination unit 2040 may detect the above action by performing the image analysis of the video data 12. For example, the determination unit 2040 compares a distribution of brightness or a distribution of color for each video frame 14 from the first video frame 14 to the second video frame 14 to detect a change in brightness or color of the imaging range of the camera 10. By doing this, the determination unit 2040 detects that the color or intensity of the light illuminating the imaging range of the camera 10 is changed or the dye is sprayed.

In a case where the image analysis is used in this manner, for example, the determination unit 2040 handles the abnormal region 30 included in the predetermined range 16 of the video frame 14 whose brightness or color is determined to be changed, as an abnormal region 30 targeted for the predetermined action by the user.

Example 3 of Predetermined Condition

Figure 6:
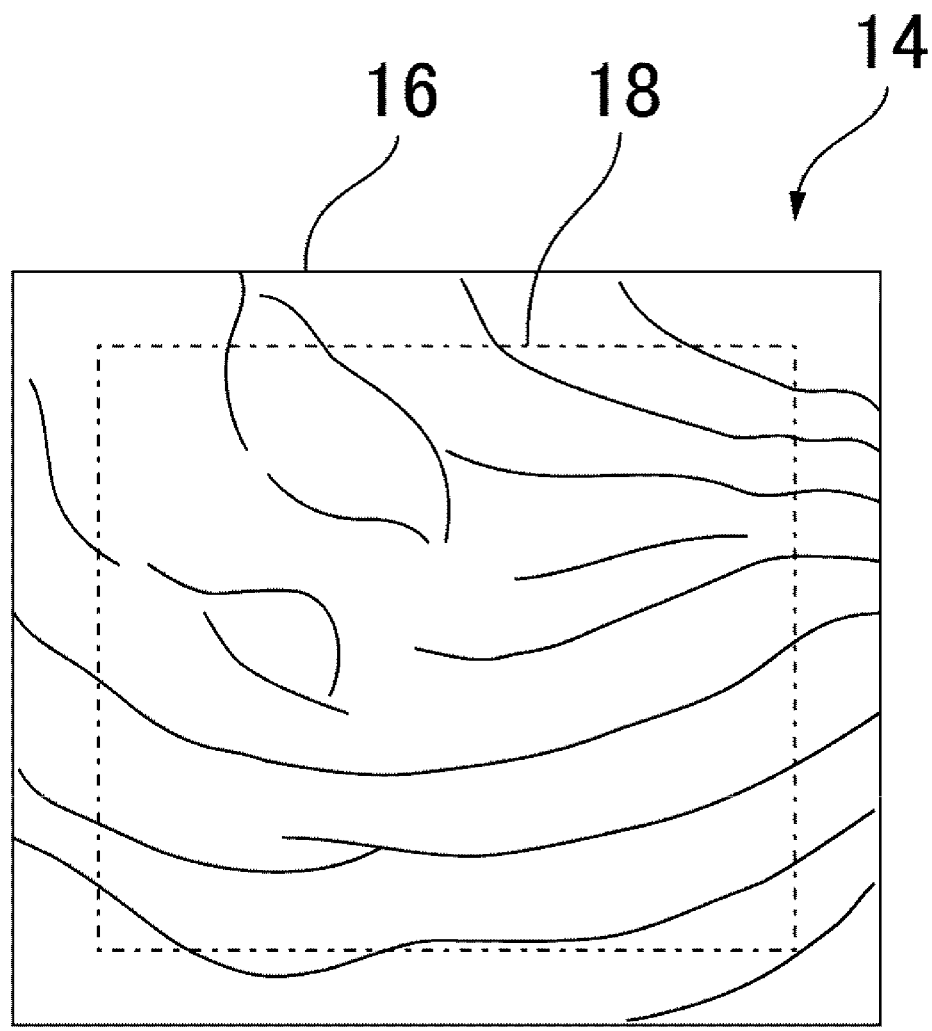
FIG. 6 is a diagram illustrating a video frame in which a second predetermined range is set.

Here, it is assumed that the predetermined range 16 is the entire image region of the video frame 14. Furthermore, it is assumed that a second predetermined range 18 smaller than the predetermined range 16 is set in the video frame 14. FIG. 6 is a diagram illustrating the video frame 14 in which the second predetermined range 18 is set. For example, the second predetermined range 18 is a range in which the center position thereof is at the center position of the video frame 14, a shape thereof has the same shape as the video frame 14, and an area thereof is 80% of the video frame 14.

A region that is inside the predetermined range 16 and outside the second predetermined range 18 can be said to be a site that is out of the center of the imaging range of the camera 10. Here, in general, when viewing a video displayed on a display device, the region closer to the center of a display screen is more easily recognized by the user. Therefore, the region that is inside the predetermined range 16 and outside the second predetermined range 18 can be considered to be a region that is difficult for the user to recognize. Accordingly, there is a high probability that the abnormal region 30 that does not fall in the predetermined range 16 is not recognized by the user.

Thus, for example, the predetermined condition is set as "the abnormal region 30 is detected from a second predetermined range 18 of at least one video frame 14 among one or more video frames 14 generated between the first video frame and the second video frame". With the predetermined condition, in a case where the abnormal region 30 falls in the predetermined range 16 but goes out of the predetermined range 16 without falling in the second predetermined range 18, the first notification by the notification unit 2060 is performed. Accordingly, under a situation where the user does not recognize the abnormal region 30 with a high probability, the first notification by the notification unit 2060 is performed. Therefore, it is possible to prevent the user from missing the abnormal region 30.

Figure 7A:
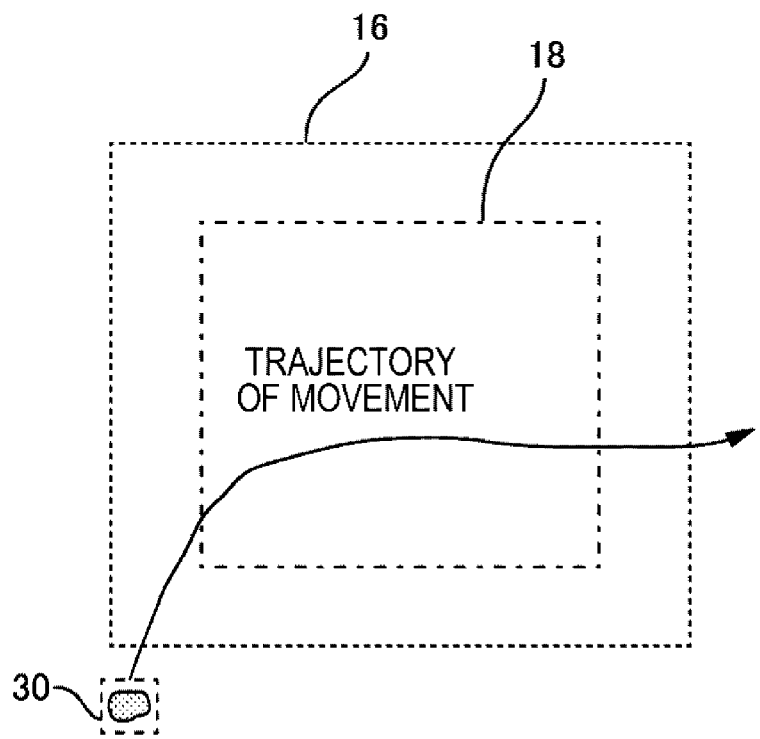
FIGS. 7A and 7B are diagrams illustrating a movement of an abnormal region in video data.
Figure 7B:
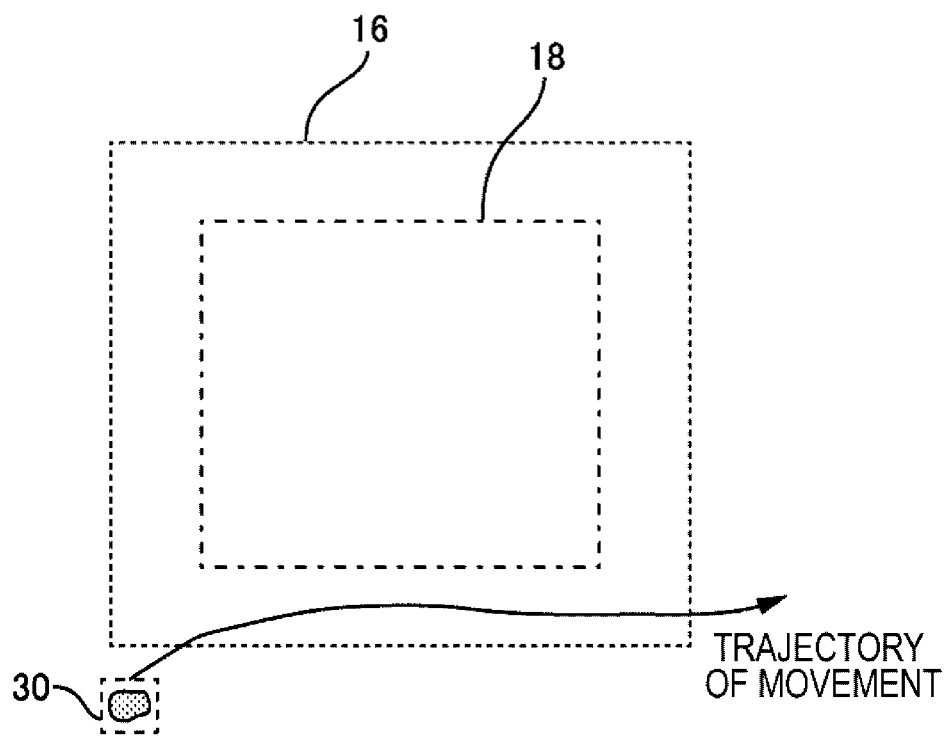

FIGS. 7A and 7B are diagrams illustrating a movement of the abnormal region 30 in the video data 12. In FIG. 7A, the abnormal region 30 falls in the predetermined range 16, then passes through the second predetermined range 18, and goes out from the predetermined range 16. Accordingly, in this case, the notification by the notification unit 2060 is not performed.

On the other hand, in FIG. 7B, the abnormal region 30 falls in the predetermined range 16 and then goes out from the predetermined range 16 without falling in the second predetermined range 18. Accordingly, in this case, the notification by the notification unit 2060 is performed.

Note that an existing technique can be used for a technique of determining whether an object included in an image is included in the predetermined range in the image.

<<Combination of Predetermined Conditions>>

The determination unit 2040 may use only any one of the above predetermined conditions, or may use any two or more of them. In the latter case, for example, the determination unit 2040 determines that "the predetermined condition is satisfied" in a case where at least one of a plurality of predetermined conditions is satisfied and determines that "the predetermined condition is not satisfied" in a case where none of the plurality of predetermined conditions is satisfied. In this case, the first notification is performed in the case where none of the plurality of predetermined conditions is satisfied.

In another example, the determination unit 2040 determines that "the predetermined condition is satisfied" in a case where all the plurality of predetermined conditions are satisfied and determines that "the predetermined condition is not satisfied" in a case where any one of the plurality of predetermined conditions is not satisfied. In this case, the first notification is performed in the case where any one of the plurality of predetermined conditions is not satisfied.

In another example, the determination unit 2040 determines that "the predetermined condition is satisfied" in a case where the number of satisfied predetermined conditions among the plurality of predetermined conditions is equal to or larger than a predetermined value and determines that "the predetermined condition is not satisfied" in a case where the number of satisfied predetermined conditions is less than the predetermined value. In this case, the first notification is performed in the case where the number of satisfied predetermined conditions is less than the predetermined value.

<First Notification by Notification Unit 2060: S112>

In a case where the above predetermined condition is not satisfied (NO in S110), the first notification by the notification unit 2060 is performed (S112). Various notifications can be employed for the first notification by the notification unit 2060. Hereinafter, specific examples thereof will be described.

Example 1 of First Notification

The notification unit 2060 causes a speaker to output a predetermined sound such as a beep sound or a voice message as the first notification. In this case, the speaker is connected to the information processing apparatus 2000. The predetermined sound may be set in advance in the notification unit 2060 or may be stored in a storage device accessible from the notification unit 2060.

<Example 2 of First Notification

The notification unit 2060 causes the display device 20 to perform a display in which the video data 12 is highlighted as the first notification. For example, the highlighting of the video data 12 is a display for displaying the frame line surrounding the video data 12 or thickening the frame line of the video data 12 that has been already displayed. In another example, the highlighting of the video data 12 is a display for blinking the video data 12 or the frame line thereof.

Figure 8A:
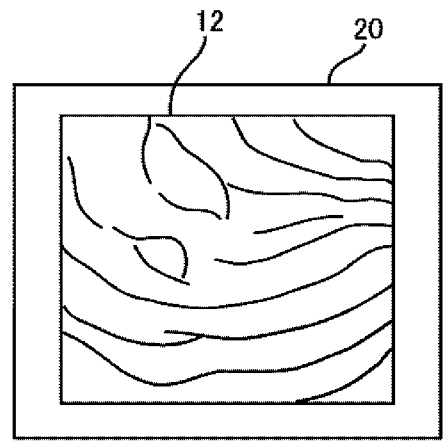
FIGS. 8A and 8B are diagrams illustrating highlighting of video data.
Figure 8B:
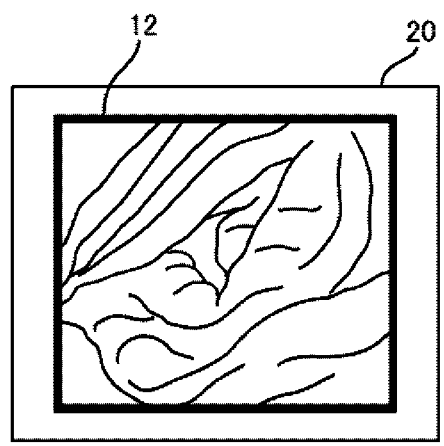

FIGS. 8A and 8B are diagrams illustrating the highlighting of the video data 12. FIG. 8A shows the display device 20 before the first notification is performed. On the other hand, FIG. 8B shows the display device 20 after the first notification is performed. In FIG. 8B, the thickness of the frame line surrounding the video data 12 is thicker than in the case of FIG. 8B.

Example 3 of First Notification

Figure 9A:
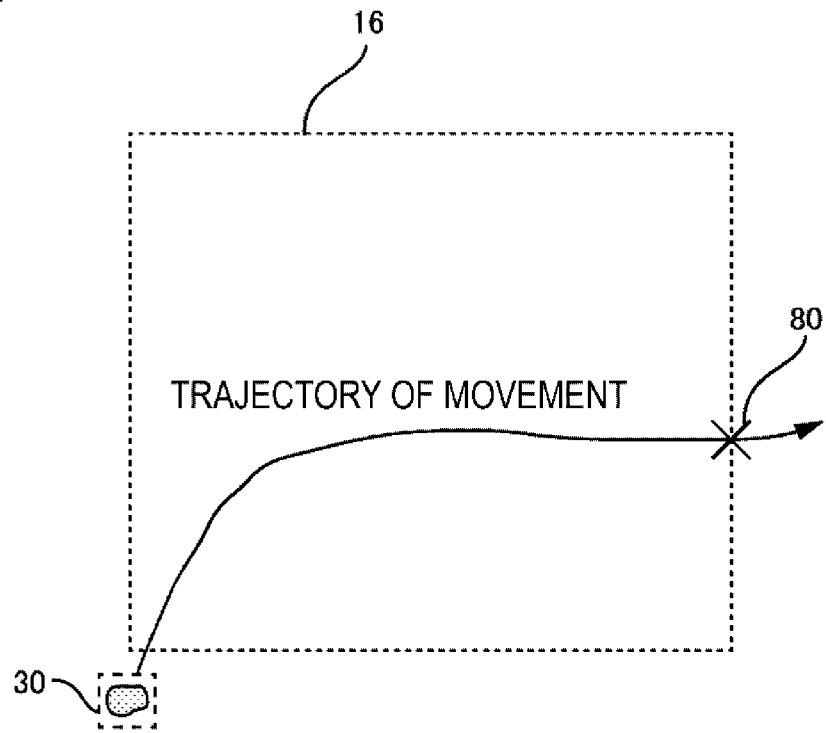
FIGS. 9A and 9B are diagrams illustrating a display indicating a position in a predetermined range where the abnormal region is last detected.
Figure 9B:
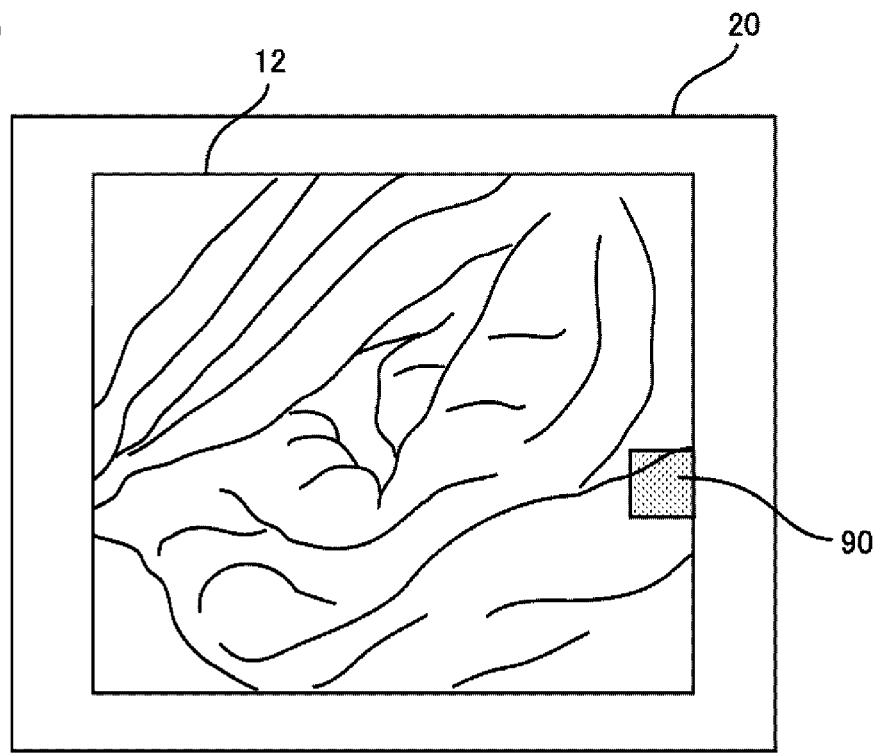

The notification unit 2060 may cause the display device 20 to display a position which is in the predetermined range 16 of the video data 12 after the first video frame and from which the abnormal region 30 is last detected, as the first notification. FIGS. 9A and 9B are diagrams illustrating a display indicating the position which is in the predetermined range 16 and from which the abnormal region 30 is last detected. In FIGS. 9A and 9B, the predetermined range 16 is the entire image region of the video frame 14. FIG. 9A represents a trajectory of the movement of the abnormal region 30 in the video data 12. FIG. 9B illustrates the first notification performed in a case where the abnormal region 30 moves along the trajectory shown in FIG. 9A.

A position of the abnormal region 30 when the abnormal region 30 goes out from the predetermined range 16 is a position 80 (refer to FIG. 9A). The notification unit 2060 causes the display device 20 to display a display 90 indicating the position 80.

Example 4 of First Notification

Figure 10A:
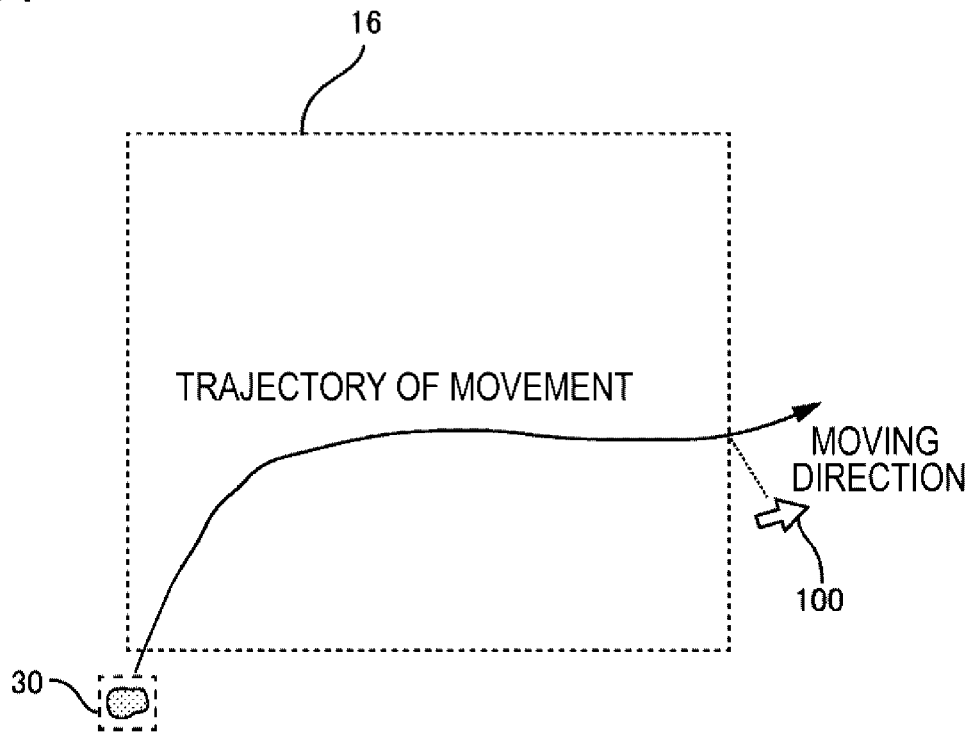
FIGS. 10A and 10B are diagrams illustrating a guide described above.
Figure 10B:
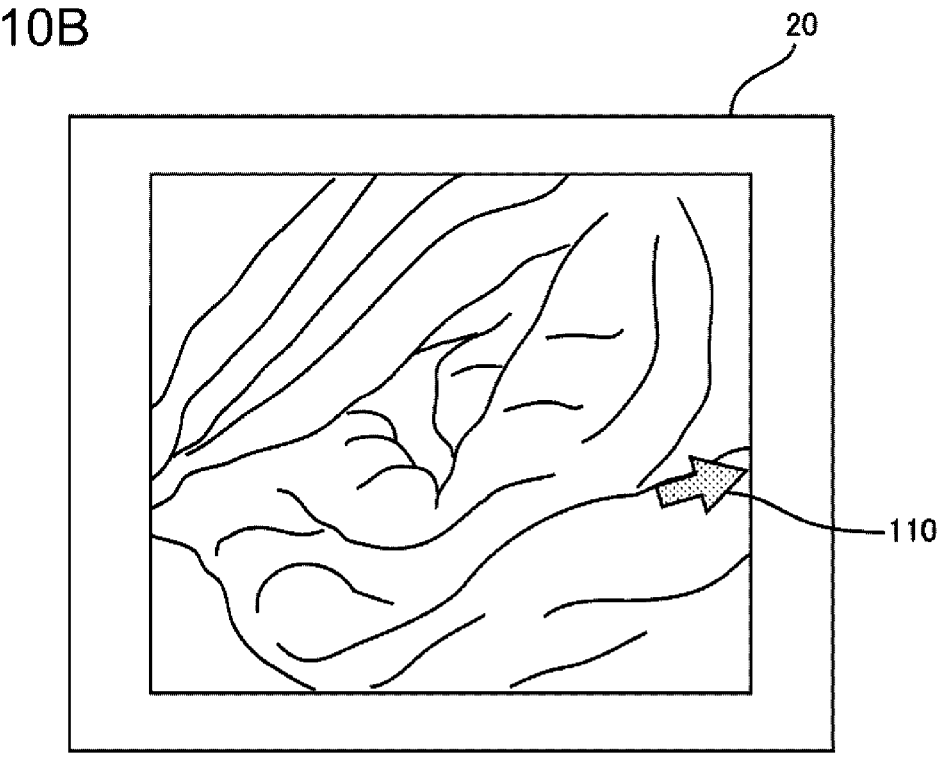

The notification unit 2060 may cause the display device 20 to display a display serving as a guide for putting the abnormal region 30, which has gone out of the predetermined range 16, into the predetermined range 16 again, as the first notification. FIGS. 10A and 10B are diagrams illustrating a guide described above. FIG. 10A represents a trajectory of movement of the abnormal region 30 in the video data 12. FIG. 10B illustrates the first notification performed in a case where the abnormal region 30 moves along the trajectory shown in FIG. 10A.

In a case where the abnormal region 30 moves out of the predetermined range 16, it is possible to put the abnormal region 30 into the predetermined range 16 again, by tracking the movement of the abnormal region 30. Accordingly, it is possible for the user to move the imaging range of the camera 10 in the same direction as the direction in which the abnormal region 30 is moved and thus to put the abnormal region 30 into the predetermined range 16.

In FIG. 10A, the moving direction of the abnormal region 30 when the region goes out from the predetermined range 16 is represented by a direction 100. In FIG. 10B, the notification unit 2060 causes the display device 20 to display a guide 110 (first notification) representing the direction 100. By doing s, it is possible for the user to easily perform an operation for putting the abnormal region 30 into the predetermined range 16 again. The display of the guide is particularly effective in the case where the predetermined range 16 is the entire image region of the video frame 14. This is because the abnormal region 30 outside the predetermined range 16 is not displayed on the display device 20 in this case.

Here, an existing technique such as a method of computing an optical flow can be used for a technique of computing a moving direction of an object detected from video data.

Example 5 of First Notification

Figure 11A:
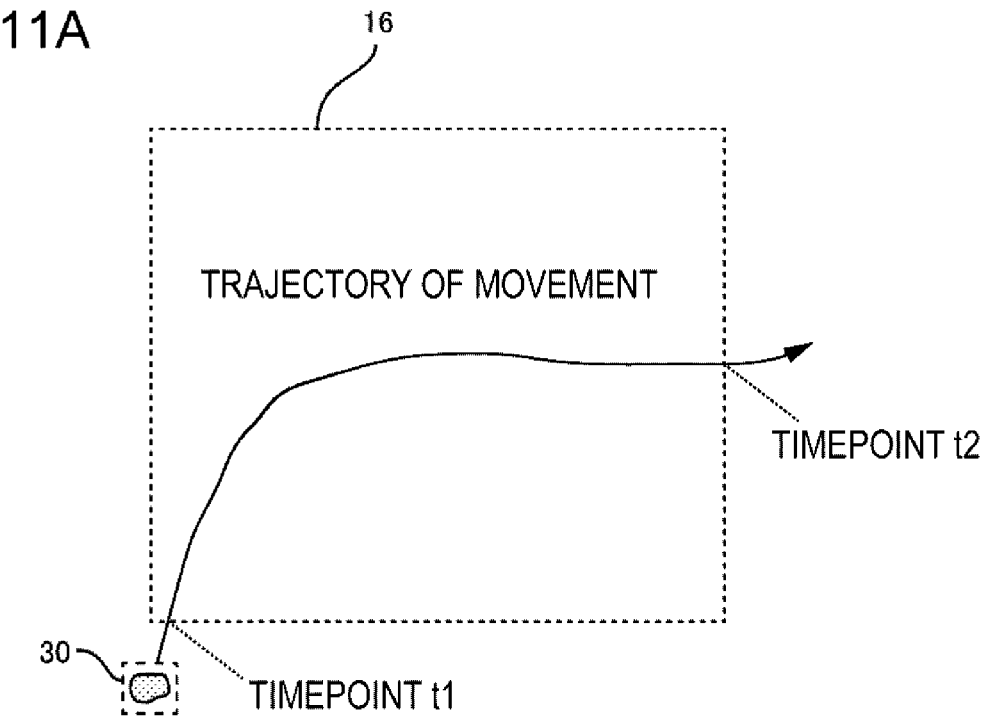
FIGS. 11A and 11B are diagrams illustrating a scene in which a video frame of which the abnormal region is included in a predetermined range is displayed as a first notification.
Figure 11B:
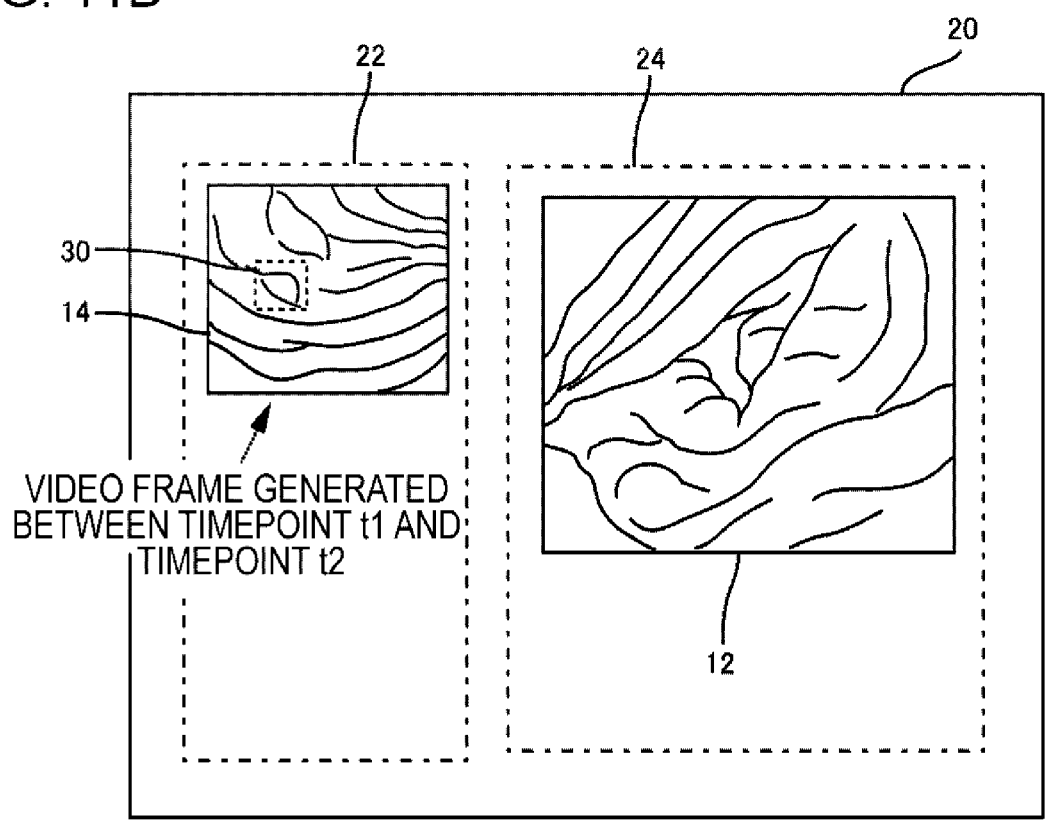

The notification unit 2060 may cause the display device 20 to display a video frame 14 which is between the first video frame and the second video frame and whose predetermined image 16 includes the abnormal region 30, as the first notification. FIGS. 11A and 11B are diagrams illustrating a scene in which the video frame 14 whose predetermined region 16 includes the abnormal region 30 is displayed as the first notification. FIG. 11A represents a trajectory of the abnormal region 30 in the video data 12. The abnormal region 30 is included within the predetermined range 16 between timepoint t1 and timepoint t2. The notification unit 2060 causes the display device 20 to display one of the video frames 14 generated between timepoint t1 and timepoint t2. FIG. 11B shows a scene in which the video frame 14 generated between timepoint t1 and timepoint t2 is displayed on the display device 20. In FIG. 11B, the information processing apparatus 2000 causes the video frame 14 displayed as the first notification to be displayed in a first region 22 of the display device 20. The information processing apparatus 2000 causes the video data 12 to be displayed in a second region 24 of the display device 20.

From the viewpoint of the user performing the examination while viewing the video data 12, it can be said that the video frame 14 to be displayed in the first region 22 is the past video frame 14 including the abnormal region 30 with a high probability of not being recognized by the user. In this manner, the video frame 14 including the abnormal region 30 with the high probability of not being recognized by the user is displayed on the display device 20 together with the video data 12. Therefore, it is possible for the user to view the first region 22 of the display device 20 and thus to recognize the abnormal region 30 later. Accordingly, it is possible to prevent the user from missing the abnormal site.

Here, there are various methods of determining the video frame 14 to be displayed in the first region 22 by the notification unit 2060. Hereinafter, the method is specifically illustrated.

<<<Method of Using Generation Timepoint>>>

The notification unit 2060 determines the last (newest) video frame 14 including the abnormal region 30 among the video frames 14 generated between the first video frame and the second video frame as the video frame 14 to be displayed in the first region 22. With this method, it is possible for the user to recognize the last position where the abnormal region 30 is imaged by the camera 10.

<<<Method of Using Accuracy Representing Abnormality>>>

The notification unit 2060 determines likelihood of that an image region representing the abnormal region 30 represents the abnormality in the body for each video frame 14 generated between the first video frame and the second video frame. For example, in a case where the abnormal region 30 is detected from the video frame 14 by the feature value matching or the template matching, the likelihood of that an image region representing the abnormal region 30 represents the abnormality in the body is represented by a degree of similarity between the image region and a feature value or a template defined in advance. The notification unit 2060 determines a video frame 14 with the highest likelihood as the video frame 14 to be displayed in the first region 22.

It can be said that the higher the likelihood of that the abnormal region 30 included in the video frame 14 represents the abnormality in the body, the more the abnormal region 30 included in the video frame 14 represents the abnormality in the body. Therefore, the user can recognize the abnormality in the body of the subject more accurately by displaying, in the first region 22, a video frame 14 whose abnormal region 30 has high likelihood of representing the abnormality in the body.

<<<Method of Using Position of Abnormal Region 30>>>

The notification unit 2060 determines a video frame 14 whose position of the abnormal region 30 is closest to the center position of the video frame 14 among each video frame 14 generated between the first video frame and the second video frame, and handles the determined video frame 14 as the video frame 14 to be displayed in the first region 22. Specifically, the notification unit 2060 computes, for each video frame 14, a distance between the abnormal region 30 included in the video frame 14 and center coordinates of the video frame 14. The notification unit 2060 determines a video frame 14 having the smallest distance as the video frame 14 to be displayed in the first region 22.

In general, in terms of an object included in an image generated by a camera, the closer the location of the object is to the center of the image, the easier it is to view the object. Therefore, the video frame 14 in which the position of the abnormal region 30 is close to the center position of the video frame 14 is displayed in the first region 22 in this manner to allow the user to easily view the abnormal region 30.

<<<Method of Using Contrast of Entire Video Frame 14>>>

The notification unit 2060 determines a video frame 14 having the largest contrast in the entire video frame 14 of each video frame 14 generated between the first video frame and the second video frame as the video frame 14 to be displayed in the first region 22. Specifically, the notification unit 2060 computes, for each video frame 14, an index value representing the contrast of the entire video frame 14. Then, the notification unit 2060 compares the computed index values to determine the video frame 14 having the largest contrast and handles the determined video frame 14 as the video frame 14 to be displayed in the first region 22. Note that, for example, Michelson contrast or the like can be used for the index value representing the contrast.

In general, it is easier to distinguish individual objects included in an image as the contrast of the image is higher. Therefore, the video frame 14 having large contrast in the entire video frame 14 is displayed in the first region 22 to allow the user to easily view the abnormal region 30.

<<<Method of Using Contrast of Image Region Representing Abnormal Region 30>>>

The notification unit 2060 may use the contrast of the image region representing the abnormal region 30 instead of the contrast of the entire video frame 14. That is, the notification unit 2060 computes an index value of the contrast of the image region representing the abnormal region 30 for each video frame 14 generated between the first video frame and the second video frame. The notification unit 2060 compares the computed index values to determine the video frame 14 having the largest contrast in the image region representing the abnormal region 30 and displays the determined video frame 14 in the first region 22.

With this method, it is easier for the user to view the inside of the abnormal region 30 since the abnormal region 30 having a large contrast is displayed on the display device 20.

<Recording of Video Frame 14>

Figure 12:
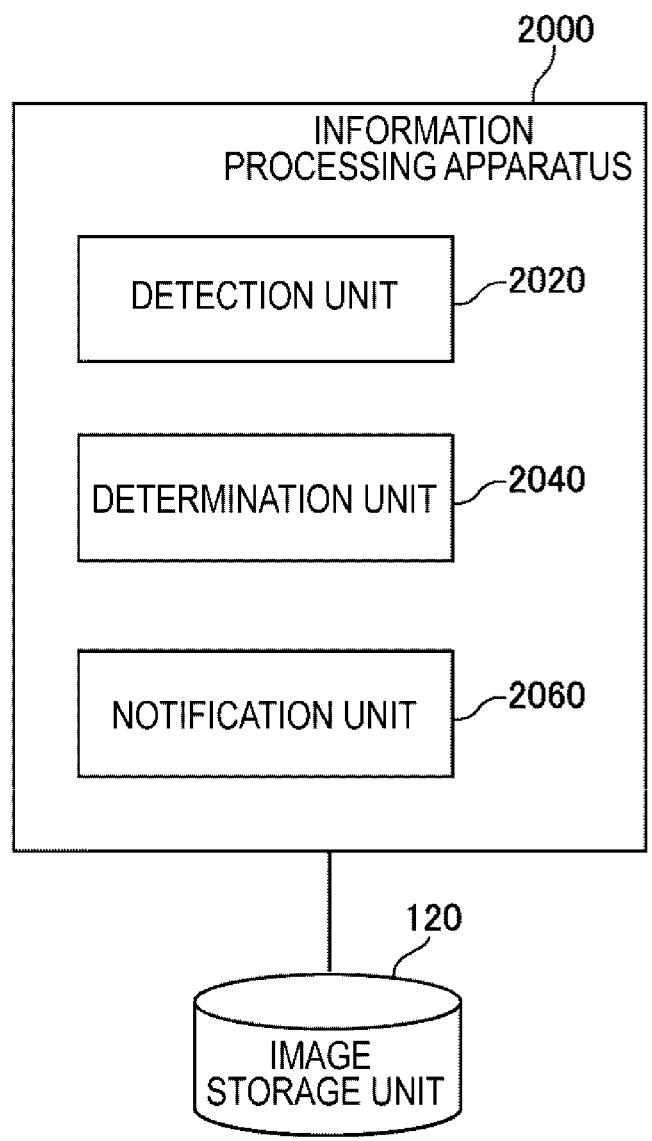
FIG. 12 is a diagram illustrating the information processing apparatus connected to an image storage unit.

The notification unit 2060 may record the video frame 14 to be displayed in the first region 22 in the storage device, while displaying the video frame 14 in the first region 22, or instead of displaying the video frame 14 in the first region 22. Hereinafter, the storage device for storing the video frame 14 is referred to as an image storage unit 120. FIG. 12 is a diagram illustrating the information processing apparatus 2000 connected to the image storage unit 120. Note that the image storage unit 120 may be provided inside the information processing apparatus 2000.

The method of determining the video frame 14 to be stored in the image storage unit 120 is the same as the method of determining the video frame 14 to be displayed in the first region described above.

The notification unit 2060 may appropriately process the video frame 14 to be recorded in the image storage unit 120. For example, the notification unit 2060 causes the image storage unit 120 to store a video frame 14 on which an image (such as a superimposition mark 60 described below) indicating the position of the abnormal region 30 is superimposed. By doing this, it is possible to easily recognize the position of the abnormal region 30 in the video frame 14. In another example, the notification unit 2060 makes an association of the video frame 14 and information specifying the position of the abnormal region 30 included in the video frame 14, and records it in the image storage unit 120.

Here, as described above, the user may operate the keyboard, the shutter button, or the like to record the video frame 14 in the storage device. For example, in general, the endoscope system is provided with the shutter button, and the user presses the shutter button and thus a video frame generated by a camera at a timing when the shutter button is pressed is recorded in the storage device.

The information processing apparatus 2000 may record the video frame 14 specified by the operation in the image storage unit 120 in response to the operation of the user in this manner. Hereinafter, the video frame 14 stored in the image storage unit 120 in response to the operation of the user in this manner is referred to as a specified storage frame. On the other hand, the video frame 14 (video frame 14 automatically recorded in the image storage unit 120 by the information processing apparatus 2000) recorded in the image storage unit 120 by the notification unit 2060 is referred to as an automatic storage frame.

The specified storage frame and the automatic storage frame are different in triggers of being recorded in the image storage unit 120 and meanings of the frames for the user. For example, the specified storage frame is a video frame 14 including an abnormal region 30 with a high probability of being recognized by the user, while the automatic storage frame is a video frame 14 including an abnormal region 30 with a high probability of not being recognized by the user. From such a difference, it is preferable that the specified storage frame and the automatic storage frame are stored in the image storage unit 120 in a mutually discriminable manner.

Figure 13:
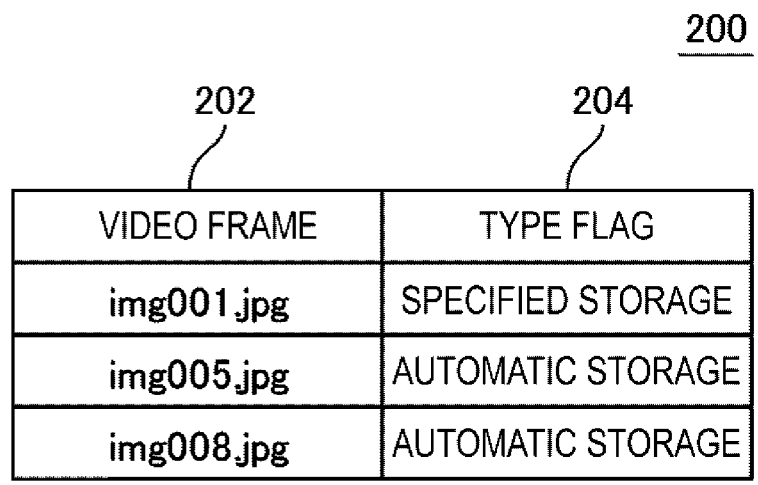
FIG. 13 is a diagram illustrating a format of information stored in the image storage unit in a table format.
Figure 14A:
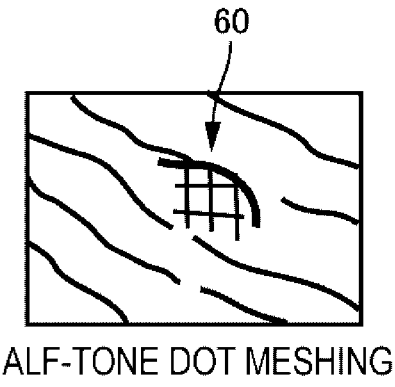
FIGS. 14A to 14F are diagrams illustrating various superimposition marks superimposed on the abnormal region.
Figure 14B:
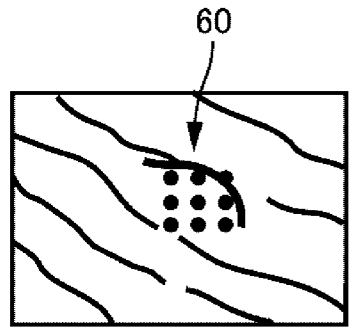
Figure 14C:
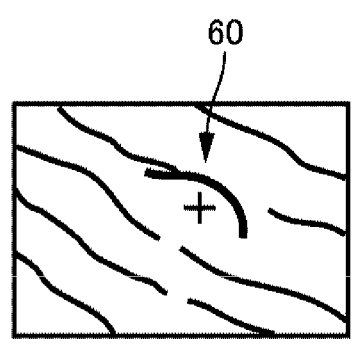
Figure 14D:
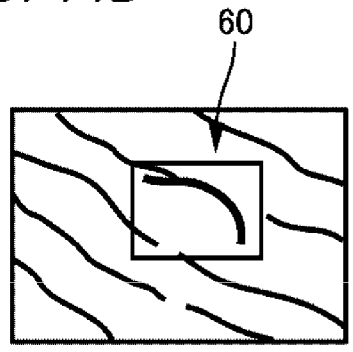
Figure 14E:
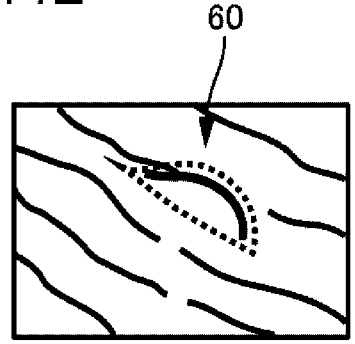
Figure 14F:
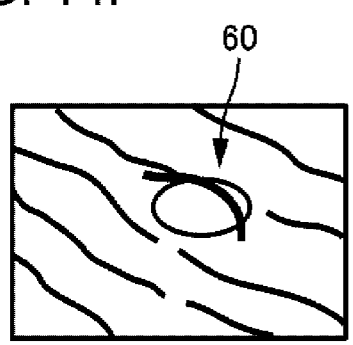

Any method of storing the specified storage frame and the automatic storage frame in the image storage unit 120 in a discriminable manner can be employed. For example, the information processing apparatus 2000 records a flag representing whether the video frame 14 is the specified storage frame or the automatic storage frame in association with the video frame 14 in the image storage unit 120. FIG. 13 is a diagram illustrating a format of information stored in the image storage unit 120 in a table format. The table shown in FIG. 13 is denoted by a table 200. The table 200 has two columns of a video frame 202 and a type flag 204. The video frame 202 represents the video frame 14 itself. The type flag 204 represents whether the video frame 14 recorded in the video frame 202 is the specified storage frame or the automatic storage frame.

Note that the method of storing the specified storage frame and the automatic storage frame in a discriminable manner is not limited to the method of providing the flag described above. For example, the information processing apparatus 2000 may records the specified storage frame and the automatic storage frame in different storage devices.

<Display Representing Abnormal Region 30>

The information processing apparatus 2000 may have a function, for a video frame 14 displayed in the first region 22, to perform a display representing the abnormal region 30 included in the video frame 14. By doing this, it is possible for the user to easily recognize the abnormal region 30 included in the video frame 14. Hereinafter, this display is referred to as a first display.

Various displays can be employed as the first display. For example, the information processing apparatus 2000 displays a predetermined mark in the abnormal region 30 so as to be superimposed on the abnormal region 30 of the video frame 14 to be displayed in the first region 22. Hereinafter, this mark is referred to as the superimposition mark. In this example, the superimposition mark is the first display. FIGS. 14A to 14F are diagrams illustrating various superimposition marks 60 superimposed on the abnormal region 30.

Figure 15A:
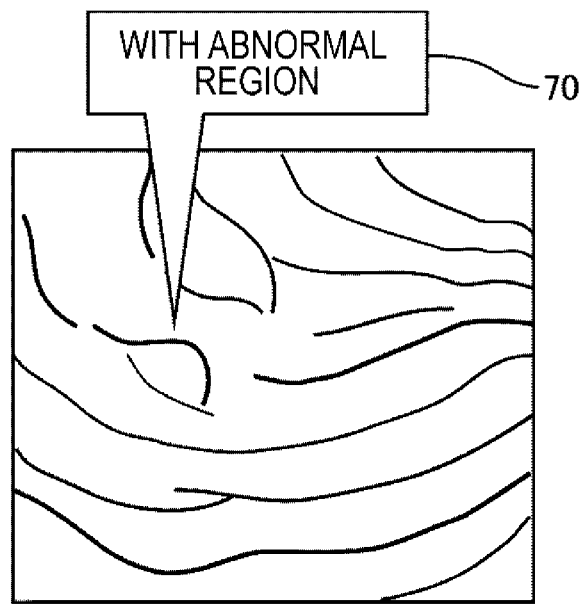
FIGS. 15A and 15B are diagrams illustrating instruction marks indicating the abnormal region.
Figure 15B:
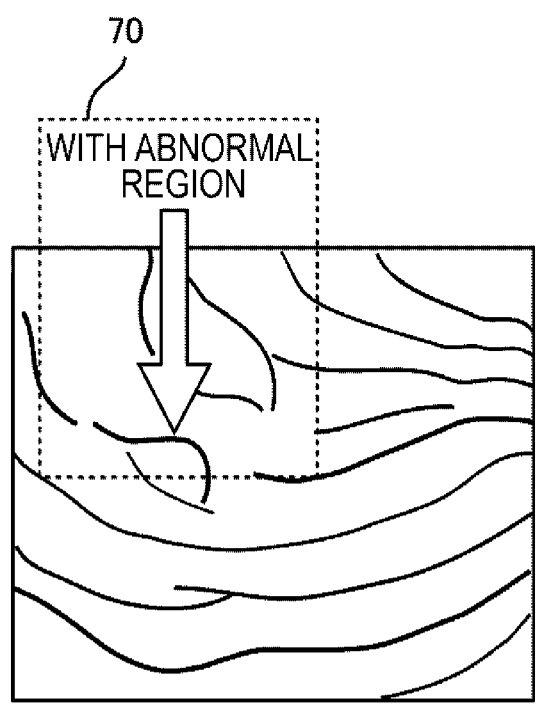

In another example, the information processing apparatus 2000 may perform the first display (hereinafter referred to as an indication mark) indicating the abnormal region 30 near the video frame 14. FIGS. 15A and 15B are diagrams illustrating indication marks 70 indicating the abnormal region 30.

Example Embodiment 2

Figure 16:
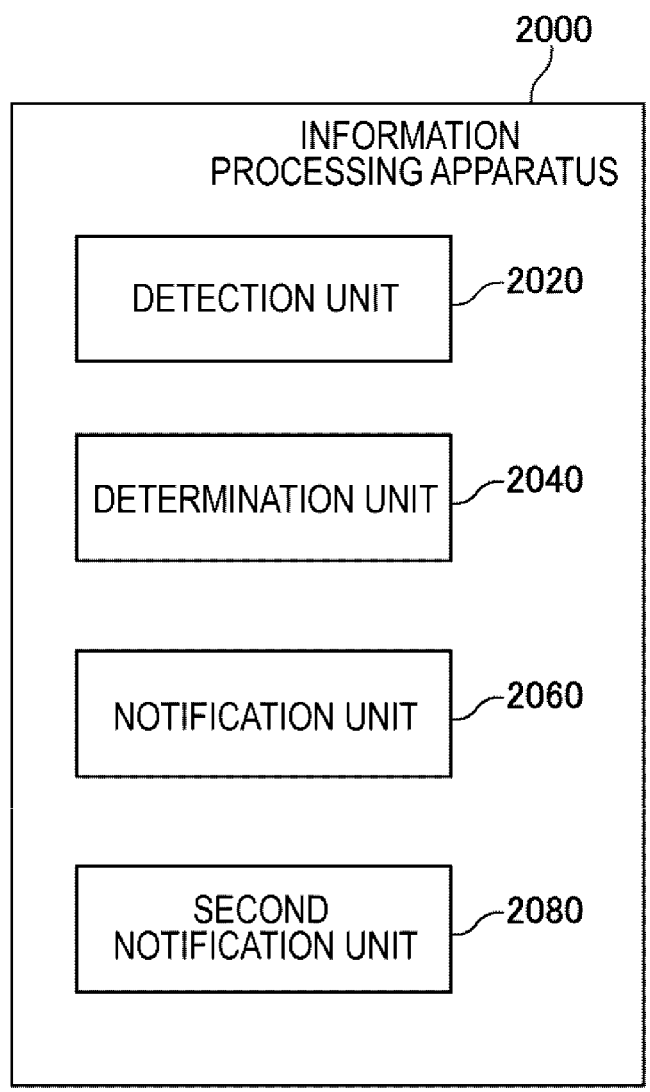
FIG. 16 is a block diagram illustrating an information processing apparatus according to an example embodiment 2.

FIG. 16 is a block diagram illustrating an information processing apparatus 2000 according to an example embodiment 2. The information processing apparatus 2000 according to the example embodiment 2 is the same as the information processing apparatus 2000 according to the example embodiment 1 except for the matters described below.

The information processing apparatus 2000 according to the example embodiment 2 has a second notification unit 2080. The second notification unit 2080 performs a predetermined notification in a case where the abnormal region 30 targeted for the first notification is detected from the predetermined range 16 of the video frame 14 generated later than the second video frame. This predetermined notification is referred to as a second notification.

Here, the fact that "the abnormal region 30 targeted for the first notification is detected from the predetermined range 16 of the video frame 14 generated later than the second video frame" means that the abnormal region 30 falls in the predetermined range 16 again, under a situation where it is highly possible that a certain abnormal region 30 goes out of the predetermined range 16 without being recognized by the user. It is considered that the user who receives the first notification from the notification unit 2060 operates the camera 10 to put the abnormal region 30 targeted for the first notification into the predetermined range 16. Therefore, the fact that the abnormal region 30 falls in the predetermined range 16 means that the user can operate the camera 10 as intended. Accordingly, when any notification is performed to the user such that the user can recognize this, the convenience of the information processing apparatus 2000 is enhanced for the user. The information processing apparatus 2000 according to the present example embodiment performs the second notification described above.

As described in the example embodiment 1, for each abnormal region 30 detected from the video data 12, in the case where the abnormal region 30 is not detected from the second video frame generated later than the first video frame in which the abnormal region 30 is detected and the predetermined condition is not satisfied, the information processing apparatus 2000 performs the first notification for the abnormal region 30. When the first notification is performed, the notification unit 2060 according to the present example embodiment records information specifying the abnormal region 30 targeted for the first notification in the storage device. This information is referred to as history information.

In a case where the abnormal region 30 is detected from the video frame 14, the second notification unit 2080 determines whether the abnormal region 30 is indicated in the history information. In a case where the abnormal region 30 is indicated in the history information, the second notification unit 2080 performs the second notification for the abnormal region 30. On the other hand, in a case where the abnormal region 30 is not indicated in the history information, the second notification unit 2080 does not perform the second notification for the abnormal region 30.

<Flow of Processing>

Figure 17:
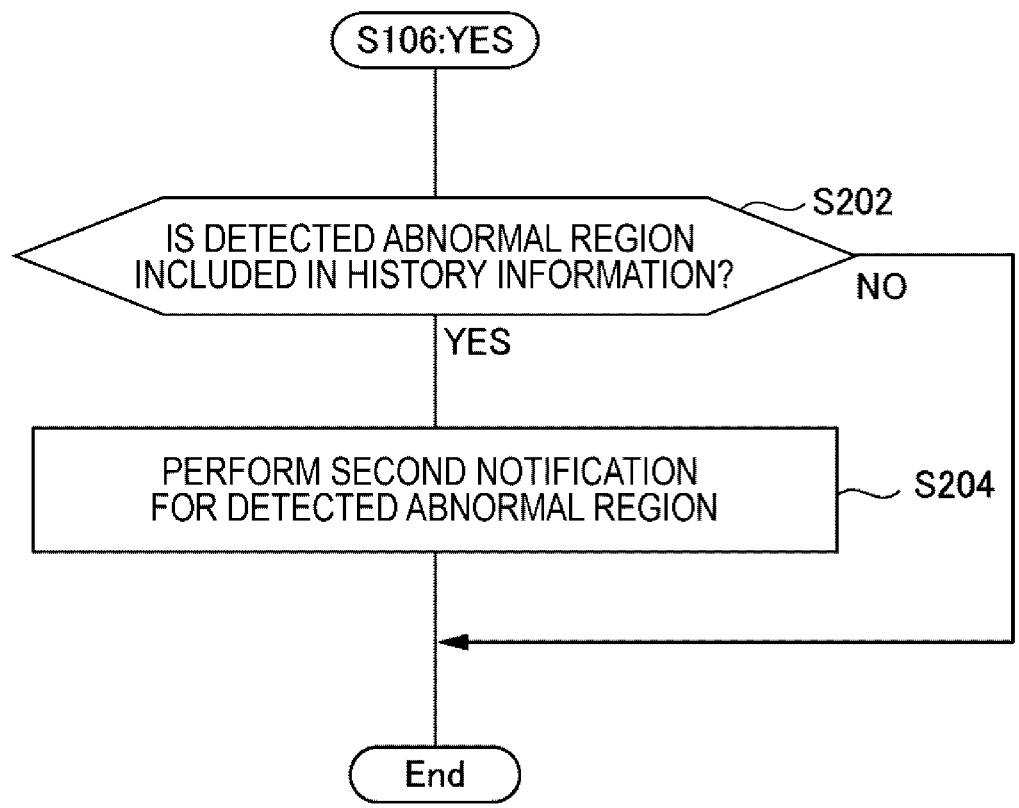
FIG. 17 is a diagram illustrating a flow of processing executed by the information processing apparatus according to the example embodiment 2.

FIG. 17 is a diagram illustrating a flow of processing executed by the information processing apparatus 2000 according to the example embodiment 2. A series of pieces of processing shown in FIG. 17 is executed after the abnormal region 30 is detected from the video frame 14 by the detection unit 2020 (YES in S106).

The second notification unit 2080 determines whether the abnormal region 30 detected by the detection unit 2020 is included in the history information (S202). In a case where the abnormal region 30 is included in the history information (YES in S202), the second notification unit 2080 performs the second notification for the abnormal region 30 (S204). On the other hand, in a case where the abnormal region 30 is not included in the history information (NO in S202), the processing of FIG. 17 ends.

<Form of Second Notification>

Various notifications can be employed as the second notification. Hereinafter, specific examples thereof will be described.

Example 1 of Second Notification

The second notification unit 2080 causes the speaker to output the predetermined sound as the second notification. The method of using the predetermined sound as the notification is as described in the example embodiment 1 as the "Example 1 of First Notification". Note that in a case where the first notification is also sound, it is preferable to use different sounds for the first notification and the second notification.

Example 2 of Second Notification

The second notification unit 2080 causes the display device 20 to highlight the video data 12 as the second notification. The method of highlighting the video data 12 is as described in the example embodiment 1 as "Example 2 of First Notification". Note that in a case where the first notification is also the highlighting of the video data 12, it is preferable to make a difference in forms for highlighting the video data 12 between the first notification and the second notification. For example, the first notification is a display to thicken the frame line of the video data 12, and the second notification is a display to cause the video data 12 to blink.

Example 3 of Second Notification

As a premise, as described as "Example 5 of First Notification", it is assumed that "a video frame 14 whose predetermined range 16 includes the abnormal region 30 and which is between the first video frame and the second video frame" is displayed in the first region 22 of the display device 20. That is, in this case, the video frame 14 whose predetermined range 16 includes the abnormal region 30 with high probability of not being recognized by the user is displayed in the first region 22.

In this case, for example, the second notification unit 2080 highlights, as the second notification, the video frame 14 including the abnormal region 30 targeted for the second notification among the video frames 14 displayed in the first region 22.

Figure 18:
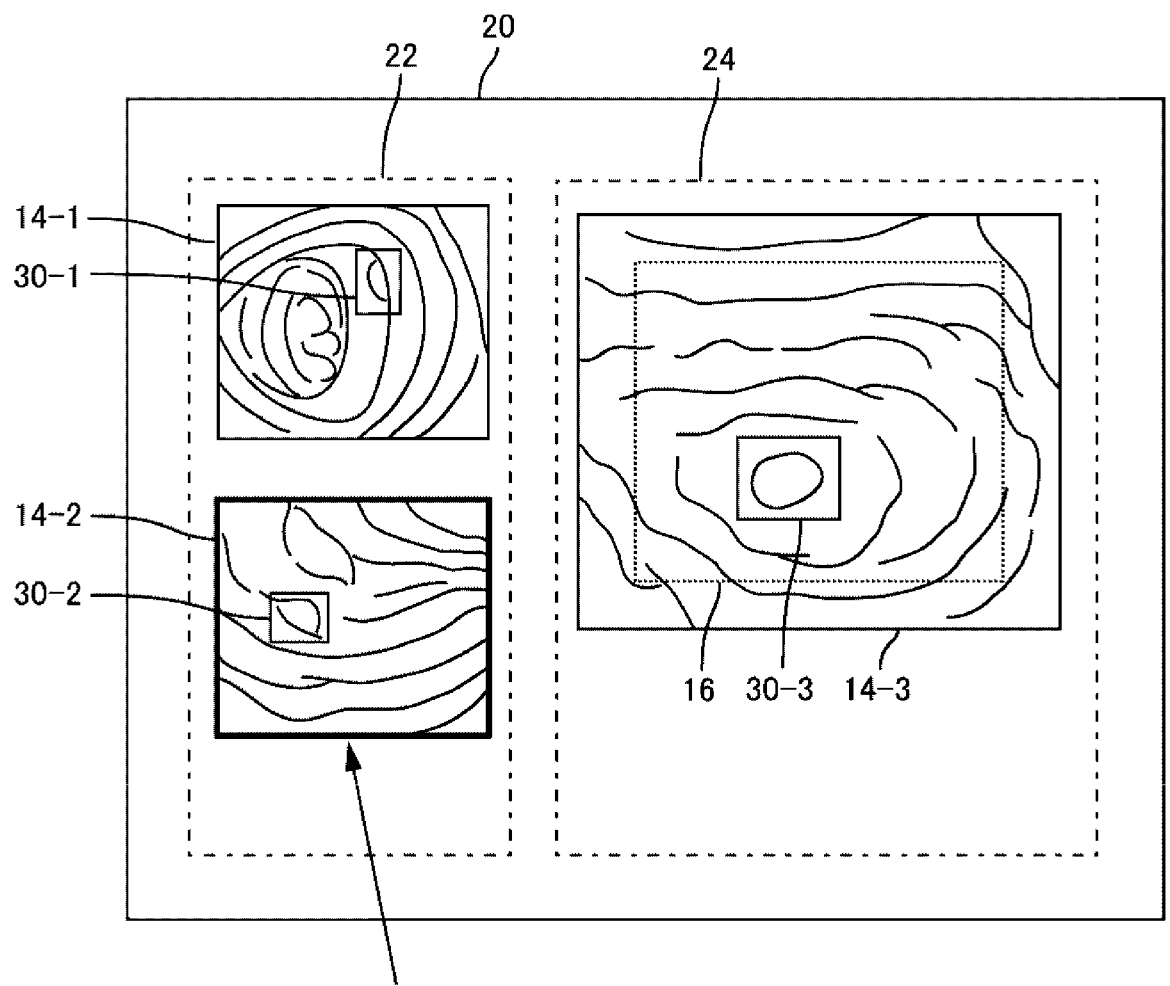
FIG. 18 is a diagram illustrating a second notification for highlighting a video frame displayed in a first region.

FIG. 18 is a diagram illustrating the second notification for highlighting the video frame 14 displayed in the first region 22. In FIG. 18, two video frames 14 (video frame 14-1 and video frame 14-2) are displayed in the first region 22. These video frames 14 include mutually different abnormal regions 30. This means that there are a plurality of abnormal regions 30 not recognized by the user.

Here, an abnormal region 30-3 is detected from a predetermined range 16 of a video frame 14-3 (the latest video frame 14 generated by the camera 10) displayed in the second region. This abnormal region 30 is assumed to be the same as the abnormal region 30-2 included in the video frame 14-2.

The second notification unit 2080 performs the highlighting to thicken the frame line of the video frame 14-2 as the second notification. By doing this, it is possible for the user to recognize that the abnormal region 30 included in the predetermined range 16 of the imaging range of the camera 10 is the same as the abnormal region 30 included in the video frame 14-2. In other words, it is possible for the user to recognize which abnormal region 30 is being currently checked using the video data 12 among the abnormal regions 30 that the user did not recognize.

<About History Information>

The notification unit 2060 records, in the history information, information that can specify the abnormal region 30 targeted for the first notification. For example, the information is a feature value of an image region representing the abnormal region 30 (for example, a parameter representing a color, a shape, or a pattern of the image region). Hereafter, a specific example of a history information configuration is shown.

FIG. 19 is a diagram illustrating the history information in a table format. The table shown in FIG. 19 is referred to as a table 300. The table 300 has two columns of an abnormal region discriminator 302 and data 304. The abnormal region discriminator 302 is a discriminator assigned to the abnormal region 30. The data 304 indicates a set of "feature value of an abnormal region 30 and discriminator of a video frame 14 in which the abnormal region 30 is detected". The notification unit 2060 generates a record indicating the set of "feature value of the abnormal region 30 and discriminator of the video frame 14 in which the abnormal region 30 is detected" in the data 304 for the abnormal region 30 targeted for the first notification when the first notification is performed, and records the record in the table 300.

The second notification unit 2080 searches for, from the table 300, a record indicating a feature value similar to the feature value of the abnormal region 30 detected from the predetermined range 16 of the video frame 14. In a case where there is the record indicating the feature value similar to the feature value of the abnormal region 30 detected from the video frame 14, the second notification unit 2080 performs the second notification. On the other hand, in a case where there is no such a record, the second notification unit 2080 does not perform the second notification.

For example, it is assumed that the feature value of the abnormal region 30 detected from the predetermined range 16 of the video frame 14 by the detection unit 2020 is v6. It is assumed that this v6 is similar to a feature value v3 shown in the table 300 of FIG. 19. In this case, when the second notification unit 2080 searches for the feature value similar to v6 from the table 300, the record in the third row of the table 300 of FIG. 19 is found as a result. Accordingly, the second notification unit 2080 performs the second notification. For example, in a case where a video frame 14 having a discriminator img3 is displayed in the first region 22 of the display device 20, the second notification unit 2080 performs the second notification for highlighting the video frame 14.

Note that the notification unit 2060 may record information obtained from a plurality of video frames 14 representing the same abnormal region 30 in one record of the history information. For example, as described above, in a case where an abnormal region 30 detected from the first video frame is tracked in each video frame 14 generated thereafter, the abnormal region 30 may be detected from the plurality of video frames 14. A set of "feature value of abnormal region 30 and discriminator of video frame 14" for each of the plurality of video frames 14 in which the abnormal region 30 targeted for the first notification is detected is recorded in one record of the table 300.

The feature value of the abnormal region 30 may differ depending on an angle at which the abnormal region 30 is imaged. Therefore, a plurality of feature values are stored for the abnormal region 30 targeted for the first notification to make it possible to determine the abnormal region 30 required to be the target for the second notification with higher accuracy.

<Hardware Configuration>

A hardware configuration of a computer that forms the information processing apparatus 2000 according to the example embodiment 2 is represented, for example, by FIG. 3 as in the example embodiment 1. However, the storage device 1080 of the computer 1000 for forming the information processing apparatus 2000 according to the present example embodiment further stores a program module for realizing the functions of the information processing apparatus 2000 according to the present example embodiment.

As mentioned above, the example embodiments according to the present invention are described with reference to drawings, but these are the examples of the present invention. The present invention may employ a combination of each example embodiment described above or various configurations other than the above.

Some or all of the above example embodiments may be described as in the following additions but are not limited to the additions.

1. An information processing apparatus, comprising:
a detection unit that detects an abnormal region of an inside of a body from a video in which the inside of the body is imaged;
a determination unit that determines whether a predetermined condition is satisfied, in a case where the abnormal region is detected from a predetermined range in a first video frame of the video and the abnormal region is not detected from the predetermined range in a second video frame of the video, the second video frame being generated later than the first video frame; and
a notification unit that performs a first notification in a case where the predetermined condition is determined to be not satisfied.

2. The information processing apparatus according to 1,
wherein the predetermined range in each video frame of the video is an entirety of the video frame.

3. The information processing apparatus according to 2,
wherein the predetermined condition is that the abnormal region is detected from a second predetermined range in any one or more of video frames generated between the first video frame and the second video frame, the second predetermined rage being included in the predetermined range and being smaller than the predetermined range.

4. The information processing apparatus according to 1,
wherein the predetermined range in each video frame of the video is a region smaller than an entirety of the video frame.

5. The information processing apparatus according to 2 or 4,
wherein the predetermined condition is that a movement velocity of the abnormal region included in the predetermined range is equal to or less than a predetermined value in the video that is from the first video frame to the second video frame.

6. The information processing apparatus according to 2 or 4,
wherein the predetermined condition is that a predetermined action by a user with respect to the abnormal region is detected after the abnormal region is detected from the predetermined range in the first video frame and before the abnormal region is determined to be not detected from the predetermined range in the second video frame.

7. The information processing apparatus according to any one of 1 to 6,
wherein the video is displayed on a display device, and
wherein the notification unit causes the display device to display a video frame including the abnormal region for which it is determined that the predetermined condition is not satisfied.

8. The information processing apparatus according to any one of 1 to 7, further comprising:
a second notification unit that performs a second notification in a case where the abnormal region is detected from a video frame generated later than the second video frame in which the abnormal region targeted for the first notification is detected.

9. The information processing apparatus according to 8,
wherein the second notification is highlighting for a video frame that is displayed on a display device and that includes the abnormal region targeted for the second notification.

10. A control method executed by a computer, the method comprising:
a detection step of detecting an abnormal region of an inside of a body from a video in which the inside of the body is imaged;
a determining step of determining whether a predetermined condition is satisfied, in a case where the abnormal region is detected from a predetermined range in a first video frame of the video and the abnormal region is not detected from the predetermined range in a second video frame of the video, the second video frame being generated later than the first video frame; and
a notification step of performing a first notification in a case where the predetermined condition is determined to be not satisfied.

11. The control method according to 10,
wherein the predetermined range in each video frame of the video is an entirety of the video frame.

12. The control method according to 11,
wherein the predetermined condition is that the abnormal region is detected from a second predetermined range in any one or more of video frames generated between the first video frame and the second video frame, the second predetermined rage being included in the predetermined range and being smaller than the predetermined range.

13. The control method according to 10,
wherein the predetermined range in each video frame of the video is a region smaller than an entirety of the video frame.

14. The control method according to 11 or 13,
wherein the predetermined condition is that a movement velocity of the abnormal region included in the predetermined range is equal to or less than a predetermined value in the video that is from the first video frame to the second video frame.

15. The control method according to 11 or 13,
wherein the predetermined condition is that a predetermined action by a user with respect to the abnormal region is detected after the abnormal region is detected from the predetermined range of the first video frame and before the abnormal region is determined to be not detected from the predetermined range in the second video frame.

16. The control method according to any one of 10 to 15,
wherein the video is displayed on a display device, and
wherein the notification step causes the display device to display a video frame including the abnormal region for which it is determined that the predetermined condition is not satisfied.

17. The control method according to any one of 10 to 16, further comprising:
a second notification step that performs a second notification in a case where the abnormal region is detected from a video frame of the video generated later than the second video frame in which the abnormal region targeted for the first notification is detected.

18. The control method according to 17,
wherein the second notification is highlighting for a video frame that is displayed on a display device and that includes the abnormal region targeted for the second notification.

19. A program that causes a computer to execute each step of the control method according to any one of 10 to 18.

The invention claimed is:

1. An information processing apparatus, comprising:
a memory configured to store instructions; and
a processor configured to executed the instructions to:
detect an abnormal region of an inside of a body from a video in which the inside of the body is imaged;
determine whether a predetermined condition is satisfied, in a case where the abnormal region is detected from a predetermined range in a first video frame of the video and the abnormal region is not detected from the predetermined range in a second video frame of the video, the second video frame being generated later than the first video frame; and
perform a first notification in a case where the predetermined condition is determined to be not satisfied.

2. The information processing apparatus according to claim 1,
wherein the predetermined range in each video frame of the video is an entirety of the video frame.

3. The information processing apparatus according to claim 2,
wherein the predetermined condition is that the abnormal region is detected from a second predetermined range in any one or more of video frames generated between the first video frame and the second video frame, the second predetermined range being included in the predetermined range and being inside and smaller than the predetermined range, and
the processor is further configured to execute the instructions to
perform the first notification in case where: the abnormal region detected in the predetermined range of the first video frame of the video is not detected from the second predetermined range in any video frame generated between the first video frame and the second video frame; and the abnormal region detected in the predetermined range of the first video frame of the video is outside the predetermined range in the second video frame.

4. The information processing apparatus according to claim 2,
wherein the predetermined condition is that a movement velocity of the abnormal region included in the predetermined range is equal to or less than a predetermined value in the video that is from the first video frame to the second video frame.

5. The information processing apparatus according to claim 2,
wherein the predetermined condition is that a predetermined action by a user with respect to the abnormal region is detected after the abnormal region is detected from the predetermined range in the first video frame and before the abnormal region is determined to be not detected from the predetermined range in the second video frame.

6. The information processing apparatus according to claim 5,
wherein the predetermined action includes an action comprising:
an input operation performed in order to record the video frame including the abnormal region in a storage unit;
a character input operation performed in order to record an opinion relating to the abnormal region;
an input operation of pointing the abnormal region or a periphery thereof; and
a predetermined input operation on an endoscope system including at least one of
(i) an action of changing a color or intensity of light irradiated to the abnormal region or the periphery thereof,
(ii) an action of performing dye spraying or coloring in the abnormal region 30 or the periphery thereof,
(iii) an action of administering a medicine to the abnormal region or the periphery thereof, and
(iv) an action of collecting a tissue of the abnormal region or the periphery thereof.

7. The information processing apparatus according to claim 1,
wherein the predetermined range in each video frame of the video is a region smaller than an entirety of the video frame.

8. The information processing apparatus according to claim 1,
wherein the video is displayed on a display device, and
wherein the processor is further configured to execute the instructions to cause the display device to display a video frame including the abnormal region for which it is determined that the predetermined condition is not satisfied.

9. The information processing apparatus according to claim 1, wherein the processor is further configured to execute the instructions
perform a second notification in a case where the abnormal region is detected from within the predetermined range in a third video frame generated later than the second video frame in which the abnormal region targeted for the first notification is not detected within the predetermined range, after detecting the abnormal region targeted for the first notification from the first video frame, and
wherein the third video frame is generated by imaging again a periphery of a position in the inside of the body at which the first video frame is imaged when the abnormal region targeted for the first notification.

10. The information processing apparatus according to claim 9,
wherein the second notification is highlighting for a video frame that is displayed on a display device and that includes the abnormal region targeted for the second notification.

11. The information processing apparatus according to claim 1,
wherein the processor is further configured to execute the instructions to determine that the predetermined condition is satisfied in a case where at least one of a plurality of predetermined conditions is satisfied and determine that the predetermined condition is not satisfied in a case where none of the plurality of predetermined conditions is satisfied.

12. The information processing apparatus according to claim 1,
wherein the processor is further configured to execute the instructions to determine that the predetermined condition is satisfied in a case where all the plurality of predetermined conditions are satisfied and determine that the predetermined condition is not satisfied in a case where any one of the plurality of predetermined conditions is not satisfied.

13. The information processing apparatus according to claim 1,
wherein the processor is further configured to execute the instructions to determine that the predetermined condition is satisfied in a case where the number of satisfied predetermined conditions among the plurality of predetermined conditions is equal to or larger than a predetermined value and determine that the predetermined condition is not satisfied in a case where the number of satisfied predetermined conditions is less than the predetermined value.

14. A control method executed by a computer, the method comprising:
detecting an abnormal region of an inside of a body from a video in which the inside of the body is imaged;
determining whether a predetermined condition is satisfied, in a case where the abnormal region is detected from a predetermined range in a first video frame of the video and the abnormal region is not detected from the predetermined range in a second video frame of the video, the second video frame being generated later than the first video frame; and
performing a first notification in a case where the predetermined condition is determined to be not satisfied.

15. The control method according to claim 14,
wherein the predetermined range in each video frame of the video is an entirety of the video frame.

16. The control method according to claim 15,
wherein the predetermined condition is that the abnormal region is detected from a second predetermined range in any one or more of video frames generated between the first video frame and the second video frame, the second predetermined range being included in the predetermined range and being inside and smaller than the predetermined range, and
the method further comprising
performing the first notification in case where: the abnormal region detected in the predetermined range of the first video frame of the video is not detected from the second predetermined range in any video frame generated between the first video frame and the second video frame; and the abnormal region detected in the predetermined range of the first video frame of the video is outside the predetermined range in the second video frame.

17. The control method according to claim 15,
wherein the predetermined condition is that a movement velocity of the abnormal region included in the predetermined range is equal to or less than a predetermined value in the video that is from the first video frame to the second video frame.

18. The control method according to claim 15,
wherein the predetermined condition is that a predetermined action by a user with respect to the abnormal region is detected after the abnormal region is detected from the predetermined range of the first video frame and before the abnormal region is determined to be not detected from the predetermined range in the second video frame.

19. The control method according to claim 14,
wherein the predetermined range in each video frame of the video is a region smaller than an entirety of the video frame.

20. The control method according to claim 14,
wherein the video is displayed on a display device, and
wherein the control method further comprises causing the display device to display a video frame including the abnormal region for which it is determined that the predetermined condition is not satisfied.

21. The control method according to claim 14, further comprising:
performing a second notification in a case where the abnormal region is detected from within the predetermined range in a third video frame of the video generated later than the second video frame in which the abnormal region targeted for the first notification is not detected within the predetermined range, after detecting the abnormal region targeted for the first notification from the first video frame, and
wherein the third video frame is generated by imaging again a periphery of a position in the inside of the body at which the first video frame is imaged when the abnormal region targeted for the first notification.

22. The control method according to claim 21,
wherein the second notification is highlighting for a video frame that is displayed on a display device and that includes the abnormal region targeted for the second notification.

23. A non-transitory computer-readable storage medium storing a program that causes a computer to execute the control method according to claim 14.

* * * * *